United States Patent [19]

Boeshore et al.

[11] Patent Number: 6,043,409
[45] Date of Patent: Mar. 28, 2000

[54] TRANSGENIC PLANTS EXPRESSING ACC OXIDASE GENES

[75] Inventors: Maury L. Boeshore, Wauconda, Ill.; Rosaline Z. Deng, Oceanside, Calif.; Kim J. Camey, Davis, Calif.; John F. Reynolds, Davis, Calif.; Glen E. Ruttencutter, DeForest, Wis.

[73] Assignee: Seminis Vegetable Seeds, Inc., Saticoy, Calif.

[21] Appl. No.: 08/793,666

[22] PCT Filed: Jun. 7, 1995

[86] PCT No.: PCT/US95/07233

§ 371 Date: Jun. 27, 1997

§ 102(e) Date: Jun. 27, 1997

[87] PCT Pub. No.: WO96/07742

PCT Pub. Date: Mar. 14, 1996

Related U.S. Application Data

[63] Continuation of application No. 08/300,335, filed as application No. PCT/US95/07233, Jun. 7, 1995.

[51] Int. Cl.[7] .............................. C12N 5/04; C12N 15/29; A01H 5/00; A01H 5/10
[52] U.S. Cl. ...................... 800/278; 536/23.2; 536/23.6; 536/23.1; 800/283; 800/285; 800/295; 800/306; 435/69.1; 435/468; 435/471; 435/410; 435/419
[58] Field of Search .................................. 536/23.2, 23.6, 536/23.1; 800/278, 283, 285, 295, 306; 435/69.1, 468, 471, 410, 419

[56] References Cited

FOREIGN PATENT DOCUMENTS

| | | | |
|---|---|---|---|
| WO 91/01375 | 2/1991 | European Pat. Off. | ........ C12N 15/29 |
| WO 92/12249 | 7/1992 | European Pat. Off. | ........ C12N 15/60 |
| WO 92/04456 | 3/1992 | WIPO . | |
| WO 92/11371 | 7/1992 | WIPO . | |
| WO 94/08449 | 4/1994 | WIPO . | |

OTHER PUBLICATIONS

Bailey, Bryan A., et al., Nucleotide Sequence of the *Nicotiana tabacum* cv Xanthi Gene Encoding 1–Aminocyclopropane–1–Carboxylate Synthase, *Plant Physiol.*, 100:1615–1616, (1992).

Botella, Jose, R., et al., Identification of two new members of the 1–aminocyclopropane–1–carboxylate synthase–encoding multigene family in mung bean, *Gene,* 123:249–253, (1993).

Dong, Jian Guo et al., Cloning of a cDNA encoding 1–aminocyclopropane–1–carboxylate synthase and expression of its mRNA in ripening apple fruit, *Planta,* 185:38–45, (1991).

Hamilton, A.J., et al., Identification of a tomato gene for the ethylene–forming enzyme by expression in yeast, *Proc. Natl. Acad. Sci., USA,* 88:7434–7437, (1991).

Huang, Pung–Ling et al., Two genes encoding 1–aminocyclopropane–1–carboxylate synthase in zucchini (*Cucurbita pepo*) are clustered and similar but differentially regulated, *Proc. Natl. Acad. Sci. USA,* 88:7021–7025, (1991).

Li, Ning et al., A functional tomato ACC synthase expressed in *Escherichia coli* demonstrates suicidal inactivation by its substrateS–adenosylmethionine, *FEBS Letters,* 306:(2,3):103–107, (1992).

Liang, Xiaowu et al., The 1–aminocyclopropane–1–carboxylate synthase gene family of *Arabidopsis thaliana, Proc. Natl. Acad. Sci, USA,* 89:11046–11050, (1992).

*EMBL ACC.* No. L27664 (Jul. 4, 1994).

Lincoln, James E., et al.,LE–ACS4, a Fruit Ripening and Wound–iduced 1–Aminocyclopropane–1–carboxylate Synthase Gene of Tomato (*Lycopersicon esculentum*), *The Journal of Biological Chemistry,* 268(26):19422–19430, (1993).

Michael, M.Z., et al., Cloning of Ethylene Biosynthetic Genes Involved in Petal Senescence of Carnation and Petunia, and their Antisense Expression in Transgenic Plants, *Curr. Plant Sci. Biotechnol. Agric,* 16:298–303, (1992).

Nakagawa, Naoki, et al., Cloning of a Complementary DNA for Auxin–Induced 1–Aminocyclopropane–1–carboxylate Synthase and Different Expression of the Gene by Auxin and Wounding, *Plant Cell Physiol.* 32(8): 1153–1163, (1991).

Nakajima, Nobuyoshi, et al., Molecular Cloning and Sequence of a Complementary DNA Encoding 1–Aminocyclopropane–1–carboxylate Synthase Induced by Tissue Wounding, *Plant Cell Physiol.* 31(7):1021–1029, (1990).

Park, Ky Young, et al., Molecular cloning of an 1–aminocyclopropane–1–carboxylate synthase from senescing carnation flower petals, *Plant Molecular Biology,* 18:377–386, (1992).

Picton, Steve, et al., Altered fruit ripening and leaf senescence in tomatoes expressing an antisense ethylene–forming enzyme transgene, *The Plant Journal,* 3(3):469–481, (1993).

Pogson, Barry J., et al., Differential Expression of Two–1–Aminocyclopropane–1–Carboxylic Acid Oxidase Genes in Broccoli after Harvest, *Plant Physiol.,* 108(2):651–657, (1995).

(List continued on next page.)

*Primary Examiner*—Lynette R. F. Smith
*Assistant Examiner*—Ousama Zaghmout
*Attorney, Agent, or Firm*—Rockey, Milnamow & Katz, Ltd.

[57] ABSTRACT

The cDNA and genomic DNA encoding the ACC oxidase of broccoli are provided along with recombinant materials containing antisense constructs of these DNA sequences to permit control of the level of ACC oxidase in and, thus, the maturation and aging of *Brassica oleracea* plants which allows one to influence, e.g., lengthen, the shelflife of these plants.

14 Claims, 15 Drawing Sheets

OTHER PUBLICATIONS

*EMBL ACC.* No. X81628 (Sep. 15, 1994).
*EMBL ACC.* No. X81629 (Sep. 15, 1994).
*EMBL ACC.* No. X81628 (Sep. 28, 1995).
*EMBL ACC.* No. X81629 (Sep. 28, 1995).
Pua, Eng–Chong, Cellular and molecular aspects of ethylene on plant morphogenesis of recalcitrant Brassica species in vitro, *Bot. Bull. Acad. Sin.* 34:191–209, (1993).
Rottman, William H., et al., 1–Aminocyclopropane–1–Carboxylate Synthase in Tomato is Encoded by a Multigene Family Whose Transcription is Induced During Fruit and Floral Senescence, *J. Mol. Biol.* 222:937–961, (1991).
Sato, Takahide, et al., The 1–Aminocyclopropane–1–carboxylate Synthase of Cucurbita, *The Journal of Biological Chemistry,* 266(6):3752–3759, (1991).
Van der Straeten, Dominique, et al., Cloning and sequence of two different cDNAs encoding 1–aminocyclopropane–1–carboxylate synthase in tomato, *Proc. Natl. Acad. Sci. USA,* 87:4859–4863, (1990).
Ververidis, Phillippos, et al., Complete Recovery in Vitro of Ethylene–Forming Enzyme Activity, *Phytochemistry,* 30(3):725–727, (1991).
Wagoner, Wendy J., et al., Superior Regeneration and Agrobacterium Infectabiity of Broccoli and Cauliflower Tissues and the Identification of a Procedure for the Generation of Transgenic Plants, *Hortscience,* 27(6):132–133, (Jun. 1992).
Wen, Chao–Ming, et al., Nucleotide Sequence of a cDNA Clone Encoding 1–Aminocyclopropane–1–Carboxylate Synthase in Mustard (*Brassica juncea*[L.] Czern & Coss)[1], *Plant Physiol.,* 103:1019–1020, (1993).
Van der Straeten, Dominique, et al., Cloning, genetic mapping , and expression analysis of an *Arabidopsis thaliana* gene that encodes 1–aminocyclopropane–1–carboxylate synthase, *Proc. Natl. Acad, Sci. USA,* 89:9969–9973, (1992).
Yip, Wing–Kin, et al., Differential accumulation of transcripts for four tomato 1–aminocyclopropane–1–carboxylate synthase homologs under various condition, *Proc. Natl. Acad. Sci. USA,* 89:2475–2479, (1992).
Eng–Chong Pua, Guek–Eng Sim and Mee–Len Chye, Isolation and sequence analysis of a cDNA clone encoding ethylene–forming enzyme in *Brassica juncea* (L.) Czern & Coss, *Plant Molecular Biology* 19:541–544, (1992).
M.S. Tian, C.G. Downs, R.E. Lill, and G.A. King, A Role for Ethylene in the Yellowing of Broccoli after Harvest, *J.Amer. Soc. Hort. Sci.* 119(2):276–281, (1994).
Athanasios Theologis, Thomas I. Zarembinski, Paul W. Oeller, Xiaowu Liang, and Steften Abel, Modification of Fruit Ripening by Suppressing Gene Expression, *Plant Physiol.* 100:549–551, (1992).

Julie Gray, Steve Picton, Junaid Shabbeer, Wolfgang Schuch and Don Grierson, Molecular biology of fruit ripening and its manipulation with antisense genes, *Plant Molecular Biology* 19:69–87, (1992).
Harry J. Klee, Maria B. Hayford, Keith A. Kretzmer, Gerard F. Barry, and Ganesh M. Kishore, Control of Ethylene Synthesis by Expression of a Bacterial Enzyme in Transgenic Tomato Plants, *The Plant Cell,* 3:1187–1193, (Nov. 1991).
A.J. Hamilton, G.W. Lycett & D. Grierson, Antisense gene that inhibits synthesis of the hormone ethylene in transgenic plants, *Nature* 346:284–287, (Jul. 1990).
Hong Wang and William R. Woodson, Nucleotide Sequence of a cDNA Encoding the Ethylene–Forming Enzyme from Petunia Corollas, *Plant Physiol.* 100:535–536, (1992).
Athanasios Theologis, One Rotten Apple Spoils the Whole Bushel: The Role of Ethylene in Fruit Ripening, *Cell,* 70:181–184,(Jul. 24, 1992).
Paul W. Oeller, Lu Min–Wong, Loverine P. Taylor, Deborah A. Pike, Athanasios Theologis, Reversible Inhibition of Tomato Fruit Senescence by Antisense RNA, *Science* 25:437–439.
Athanasios Theologis, Paul W. Oeller, Lu–Min Wong, William H. Rottmann, and David M. Gantz, Use of a Tomato Mutant Constructed With Reverse Genetics to Study Fruit Ripening, A Complex Developmental Process, *Developmental Genetics* 14:282–295, (1993).
Michael J. Holdsworth, C.R. Bird, J. Ray, W. Schuch and Donald Grierson, Structure and expression of an ethylene–related mRNA from tomato, *Nucleic Acids Research* IRL Press Limited, Oxford, England 731–739.
Hong Wang and William R. Woodson, A Flower Senescence–Related mRNA from Carnation Shares Sequence Similarity with Fruit Ripening–related mRNAs Involved in Ethylene Biosynthesis, *Plant Physiol.* 96:1000–1001, (1991).
Claudine Balague, Colin F. Watson, Andrew J. Turner, Pierre Rouge, Steve Picton, Jean–Claude Pech, and Don Grierson, Isolation of a ripening and wound–induced cDNA from *Cucumis melo* L. encoding a protein with homology to the ethylene–forming enzyme, Eur. J. Biochem. 212:27–34, (1993).
Jerry L. Slightom, Custom polymerase–chain–reaction engineering of a plant expression vector, *Gene* 100:251–255, (1991).
T.M. Klein, E.D. Wolf, R. Wu, & J. C. Sanford, High–velocity microprojectiles for delivering nucleic acids into living cells, *Nature* 327:70–73, (1987).
Pua et al. Plant Molecular Biology. 1992. vol. 19: 541–544.
Srivastava et al. Plant Cell Reports. 1988. vol. 7: 504–507.
Spanu et al. EMBO J. 1991. Aug. issue. vol. 10: 2007–2013.

FIG. 1

```
  1 ATGGAGAAGAACATTAAGTTTCCAGTTGTGTAGACTTGTCTCCAAGCTCATTGGTGAAGAGAGACCAAACCATGGCTTTGATCAACGATGCTTGTGAGAATT  100
    M  E  K  N  I  K  F  P  V  V  D  L  S  K  L  I  G  E  E  R  D  Q  T  M  A  L  I  N  D  A  C  E  N  W

101 GGGGCTTCTTTGAGATAGTGAACCATGGTTTACCACATGATTTGATGGACAACGTCGAGAAGATGACAAAGGAACATTACAAGATATCAATGGAACAAAA  200
    G  F  F  E  I  V  N  H  G  L  P  H  D  L  M  D  N  V  E  K  M  T  K  E  H  Y  K  I  S  M  E  Q  K

201 GTTCAACGACATGCTCAAATCAAAGGTTTGGAAAATCTTGAGAGAGAAGTTGAGGATGTTGATTGGGAAAGCACTTTCTACCTTCGTCATCCCCTCAG  300
    F  N  D  M  L  K  S  K  G  L  E  N  L  E  R  E  V  E  D  V  D  W  E  S  T  F  Y  L  R  H  L  P  Q

301 TCCAATCTCTACGACATTCCTGATATGTCTGATGAATACCGGACGGCCATGAAAGATTTTGGAAAGAGATTGGAGAATCTTGCTGAGGATTGTTGATC  400
    S  N  L  Y  D  I  P  D  M  S  D  E  Y  R  T  A  M  K  D  F  G  K  R  L  E  N  L  A  E  D  L  L  D  L

401 TATTGTGTGAGAATTAGGGTTAGAGAAAGGGTACTTGAAGAAAGGTCCAACCTTTGGAGACTAAGGTGAGCAACTATCCAGC  500
    L  C  E  N  L  G  L  E  K  G  Y  L  K  K  V  F  H  G  T  K  G  P  T  F  G  T  K  V  S  N  Y  P  A

501 TTGTCCTAAGCCAGAGATGATCAAAGGTCTTAGGGCCCACACTGATGCAGGAGGCATCATCTTGTTTCAAGATGACAAGGTCAGTGGTCTCCAGCTT  600
    C  P  K  P  E  M  I  K  G  L  R  A  H  T  D  A  G  G  I  I  L  F  Q  D  D  K  V  S  G  L  Q  L

601 CTTAAAGATGGTGACTGGATTGATGTTCCTCCACTCAACCACTCTATTGTCATCAATCTTGGTGACCAACTTGAGGTGATAACCAACGGCAGTACAAGA  700
    L  K  D  G  D  W  I  D  V  P  P  L  N  H  S  I  V  I  N  L  G  D  Q  L  E  V  I  T  N  G  R  Y  K  S

701 GTTGATGCATCGTGTGGTGACTCAAGAAGAAGGAAACAGAAATGTCAATTGCATCTTTCTACAACCCGGAAGCTGAGATCTCTCCAGCTTCATC  800
    V  M  H  R  V  V  T  Q  K  E  G  N  R  M  S  I  A  S  F  Y  N  P  G  S  D  A  E  I  S  P  A  S  S

801 GCTTGCCTGTAAAGAAACCGAGTACCCAAGTTTTGTTTTTGATGACTACATGAAGCTCTATGCTGGGGTCAAGTTCAGCCTAAGGAGCCACGGTTCGAG  900
    L  A  C  K  E  T  E  Y  P  S  F  V  F  D  D  Y  M  K  L  Y  A  G  V  K  F  Q  P  K  E  P  R  F  E

901 GCAATGAAGAATGCTAATGCAGTTACAGAATTGAACCCAACAGCAGCCGTAGAGACTTTCTAA  963
    A  M  K  N  A  N  A  V  T  E  L  N  P  T  A  A  V  E  T  F  *
```

FIG. 2A

```
        Nco I                                                  Nco I
     GAGAGCCATGGAGAAGAACATTAAGTTTCCAGTTGTAGACTTGTCCAAGCTCATTGGTGAAGAGAGAGACCAAACAATGGCTTTGATCAACGATGC<----RMM470
     GAGAGCCATGGAGAAGAACATTAAGTTTCCAG<----RMM389          .         .         .         .         .
B. oler ATGGAGAAGAACATTAAGTTTCCAGTTGTAGACTTGTCCAAGCTCATTGGTGAAGAGAGAGACCAAACCATGGCTTTGATCAACGATGCTTGTGAGAATT
B. junc ---------+---------+---------+---------+---------+---------+---------+---------+---------+---------+  100
B. oler  M  E  K  N  I  K  F  P  V  V  D  L  S  K  L  I  G  E  E  R  D  Q  T  M

FIG. 2B

```
     TTGTCCTAAGCCAGAGATGATCAAAGGTCTTAGGGCCCACACTGATGCAGGAGGCATCATCTTGTTTCAAGATGACAAGGTCAGTGGTCTCCAGCTT
501  ---------+---------+---------+---------+---------+---------+---------+---------+---------+---------+  600
                                                            C                                    C
      C   P   K   P   E   M   I   K   G   L   R   A   H   T   D   A   G   G   I   I   L   L   F   Q   D   D   K   V   S   G   L   Q   L
                                A                                                                                           T

CTTAAAGATGGTGACTGTGATTGATGTCCTCCACTCAACCACTCTATTGTCATCAATCTTGGTGACCAACTTGAGGTGATAACCAACGGCAGGTACAAGA
601  ---------+---------+---------+---------+---------+---------+---------+---------+---------+---------+  700
                                                                                                    T
      L   K   D   G   D   W   I   D   V   P   P   L   N   H   S   I   V   I   N   L   G   D   Q   L   E   V   I   T   N   G   R   Y   K   S

GTGTGATGCATCGTGTGTGACTCAGAAAGAAGGAAACAGAATGTCAATTGCATCTTTCTACAACCCGGGAAGCGATGCTGAGATCTCTCCAGCTTCATC
701  ---------+---------+---------+---------+---------+---------+---------+---------+---------+---------+  800
        A      C
      V   M   H   R   V   V   T   Q   K   E   G   N   R   M   S   I   A   S   F   Y   N   P   G   S   D   A   E   I   S   P   A   S   S
      ***M**

GCTTGCCTGTAAAGAAACCGAGTACCCAAGTTTTGTTTTTGATGACTACATGAAGCTCTATGCTGGGGTCAAGTTTCAGCCTAAGGAGCCACGGTTCGAG
801  ---------+---------+---------+---------+---------+---------+---------+---------+---------+---------+  900
                G                                                                                         C
      L   A   C   K   E   T   E   Y   P   S   F   V   F   D   D   Y   M   K   L   Y   A   G   V   K   F   Q   P   K   E   P   R   F   E
                                                       CGGCATCCTGAAAGATTTTGTGGTACCTCAAA<----RMM480
                                                       CGGCATCCTGAAAGATTTTTGTGGATCCTCAAACTCGC<----RMM391
                                                                            NcoI

GCAATGAAGAATGCTAATGCAGTTACAGAATTGAACCCAACAGCAGCCGTAGAGACTTTCTAAAAACAAAGTGAGTTTGAGCG
901  ---------+---------+---------+---------+---------+---------+---------+---------+-----
                                        G
      A   M   K   N   A   N   A   V   T   E   L   N   P   T   A   A   V   E   T   F   *
```

FIG. 3A

```
              NcoI                                                                                    NcoI
      GAGAGAGAGCCATGGAGAAGAACATTAAGTTTCCAG<-----RMM389
3-1   GAGAGAGAGCCATGGAGAAGAACATTAAGTTTCCAGTTGTCCAGTTGTAGACTTGTCCAAGCTCATTGGTGAAGAGAGAGACCAAACCATGGCTTTGATCAACGATGC   100
      ---------+---------+---------+---------+---------+---------+---------+---------+---------+---------+
G-3   GAGAGAGAGCCATGGAGAAGAACATTAAGTTTCCAGTTGTCCAGTTGTAGACTTGTCCAAGCTCATTGGTGAAGAGAGAGACCAAACCATGGCTTTGATCAACGATGC   100

101   TTGTGAGAATTGGGGCTTCTTTGAGTTGTGAGGTACAAGCATATATATGTGATTATATCTAGCTTTTTTGAGTTTGTGTACTTAATTGGTAATGTGGATCTTTTTGTTT   200
      ---------+---------+---------+---------+---------+---------+---------+---------+---------+---------+
101   TTGTGAGAATTGGGGCTTCTTTGA
                              INTRON I
                                       NcoI
201   GGTGGTTAACTTGATTTTCCAGATAGTGAACCATGGTTTACCACACATGATTTGATGGACAACGTCGAGAAGATGACAAAGGAACATTACAAGAGATATCAATG   300
      ---------+---------+---------+---------+---------+---------+---------+---------+---------+---------+
201                   GATAGTGAACCATGGTTTACCACACATGATTTGATGGACAACGTCGAGAAGATGACAAAGGAACATTACAAGAGATATCAATG   300

301   GAACAAAAGTTCAACGACATGCTCAAATCAAAAGGTTTGGAAAATCTTGAGAGAAGTTGAGGATGTTGATTGGGAAAGCACTTTCTACCTTCGTCATC   400
      ---------+---------+---------+---------+---------+---------+---------+---------+---------+---------+
301   GAACAAAAGTTCAACGACATGCTCAAATCAAAAGGTTTGGAAAATCTTGAGAGAAGTTGAGGATGTTGATTGGGAAAGCACTTCTACCTTCGTCATC   400

401   TCCCTCAGTCCAATCTCTACGACATTCCTGATGAATGTCTGATATGTCTATATATTTTCTTCATAAAATCAACTTTAAATCATATGTTATGG   500
      ---------+---------+---------+---------+---------+---------+---------+---------+---------+---------+
401   TCCCTCAGTCCAATCTCTACGACATTCCTGATGAATGTCTGATATGTCTGATGAATACCGG
                                                                    INTRON II

501   TAACCAAAAAATATCATATGTTATATCCCCTTTAAAAGGGCCACTCTGCCACTTTTACCTATATATTAAAAGATTTTGTGATATTTATTTCTAAACAAA   600
      ---------+---------+---------+---------+---------+---------+---------+---------+---------+---------+
501                                                                                                         600

601   ATAACTATACTTTGTTAGTTAGTAAAAAACAGTTTTAAGGAATTGTTTTCACTTTAGAACCTCTAATCCTTTTGTAATGAAAATAAAGTTGAGAAGAA   700
      ---------+---------+---------+---------+---------+---------+---------+---------+---------+---------+
601                                                                                                         700

701   ACGTCTAAAATTTAACACACTTATTTGAAAGAGGCATACTGAAAATGTTTTATTTTGCAGGACGGCCATGAAAGATTTTGGGAAGAGAGATTGGAGAATCT   800
      ---------+---------+---------+---------+---------+---------+---------+---------+---------+---------+
701                                                                    ACGGCCATGAAAGATTTTGGGAAGAGAGATTGGAGAATCT   800

801   TGCTGAGGATTTGTTGGATCTATTGTGTGAGAATTAGGGTTAGAGAAAGGTACTTGAAGAAAAGGTCCAACCTTTGGGACT   900
      ---------+---------+---------+---------+---------+---------+---------+---------+---------+---------+
801   TGCTGAGGATTTGTTGGATCTATTGTGTGAGAATTAGGGTTAGAGAAAGGTACTTGAAGAAAAGGTCCAACCTTTGGGACT   900
```

FIG. 3B

```
901  AAGGTGAGCAACTATCCAGCTTGTCCTAAGCCAGAGATGATCAAAGGTCTTAGGGCCCACACTGATGCAGGAGGCATCATCTTGTTTCAAGATGACA  1000
     ----+----+----+----+----+----+----+----+----+----+----+----+----+----+----+----+----+----+----+----
901  AAGGTGAGCAACTATCCAGCTTGTCCTAAGCCAGAGATGATCAAAGGTCTTAGGGCCCACACTGATGCAGGAGGCATCATCTTGTTTCAAGATGACA  1000

1001 AGTCAGTGGTCTCCAGCTTCCAGCTTCTTAAAGATGTGACTGGATTGATGTTCCTCCACTCTATTGTCATCAATCTTGGTGACCAACTTGAGGTATG  1100
     ----+----+----+----+----+----+----+----+----+----+----+----+----+----+----+----+----+----+----+----
1001 AGGTCAGTGGTCTCCAGCTTCCAGCTTCTTAAAGATGGTGACTGGATTGATGTTCCTCCACTCTATTGTCATCAATCTTGGTGACCAACTTGAGGT

1101 ATATGTTCACACCACATTTCAAAAAAATCTCTTGTTAAAAAATCCAATGTTCGGTTATTGAGTATTGGTTTGTTCGGGTTTGATGTAACTGGAAAAAT  1200
     ----+----+----+----+----+----+----+----+----+----+----+----+----+----+----+----+----+----+----+----
1101                                           INTRON III

1201 GATTAGTAAATGTTATAACAGAGCTTATAAACTAGAAGAGCAACGTTTCCAACCTCAAATGGCTTTGGACATTCATTGTATTGTTCTCAAATGGTTT  1300
     ----+----+----+----+----+----+----+----+----+----+----+----+----+----+----+----+----+----+----+----
1201

1301 CTTTGGAAAAGCTAAGGTTTAACTGGAAATATTTTCCTTATTGAATGTAGTGATAACCAACGGCAGTACAAGAGTGTGATGCATCGTGTGGTGACT  1400
     ----+----+----+----+----+----+----+----+----+----+----+----+----+----+----+----+----+----+----+----
1301                                                 GATAACCAACGGCAGTACAAGAGTGTGATGCATCGTGTGGTGACT

1401 CAGAAAGAAGGAAACAGAATGTCAATTGCATCTTTCTACAACCCGGGAAGGCGATGCTGAGATCTCTCCAGCTTCATCGCTTGCCTGTAAAGAAACCGAGT  1500
     ----+----+----+----+----+----+----+----+----+----+----+----+----+----+----+----+----+----+----+----
1401 CAGAAAGAAGGAAACAGAATGTCAATTGCATCTTTCTACAACCCGGGAAGGCGATGCTGAGATCTCTCCAGCTTCATCGCTTGCCTGTAAAGAAACCGAGT

1501 ACCCAAGTTTGTTTTGATGACTACATGAAGCTCTATGCTGGGGTCAAGTTTCAGCTGAAGTTTCAGCCTAAGGAGCCACGGTTCGAGGCAATGAAGAATGCTAATGCAGT  1600
     ----+----+----+----+----+----+----+----+----+----+----+----+----+----+----+----+----+----+----+----
1501 ACCCAAGTTTGTTTTGATGACTACATGAAGCTCTATGCTGGGGTCAAGTTTCAGCTGAAGTTTCAGCCTAAGGAGCCACGGTTCGAGGCAATGAAGAATGCTAATGCAGT

1601 TACAGAATTGAACCCAACAGCAGCCGTAGAGACTTTCTAAAAACAAAGTGAGTTTGAGCGCCGAAACGAAAGAAACAAAATGTGTTTGTGTTGTGTGTTTA  1700
     ----+----+----+----+----+----+----+----+----+----+----+----+----+----+----+----+----+----+----+----
1601 TACAGAATTGAACCCAACAGCAGCCGTAGAGACTTTCTAAAAACACCTAGGAGTTTGA

NcoI
1701 CGTCAATAAGTTAAAGACTGATATTATTGTTGATATAATTAAGATGTCTGGCGGTTAATTGTTGGTCCATGG  1772
     ----+----+----+----+----+----+----+----+----+----+----+----+----+----+----+----+
1701                      CCGCCAATTAACAACCAGTACCACCAAATTTCACACCC <----RMM390
```

EFE3.7 A.S. CASSETTE

EFE3.3 SENSE CASSETTE

FIG. 9

```
B. oleracea  ..........  ..........  ..........  ..........  ..........  ..GAGAGAGA  GCCATGGAGA  AGAACATTAA  GTTTCCAGTT  GTAGACTTGT
C. melo      ..........  ..........  ..........  ..........  ..........GC  ACAAACCAAA  TCTTGTATCT  ACA..AAAAG  AAATGGCTGT  CTTTCCTATC  ATCAACTTGG B. oleracea  CCAAGCTC..  ........ATT  GGTGAAGAGA  GAGACCAAAC  CATGGCTTTG  ATCAACGATG  CTTGTGAGAA  TTGGGGCTTC  TTTGAGATAG  TGAACCATGG
C. melo      AAAACATTC..  ........AAT  GATGATGGTA  GAGCTAAGAT  ATTGGAGCAA  ATTGAAGATG  CCTGCCAAAA  TTGGGGTTTC  TTTGAGTTGG  TGAACCATGG B. oleracea  TTTACCACAT  GATTTGATGG  ACAACGTCGA  AAGGAACATT  ACAAGATATC  AAGGAACAA   AAGTTCAACG  ACATGCTCAA  ATCAAAAGGT
C. melo      GATCCCACAT  GAGTTTTTAG  ACATGGTGGA  AGAGATGACA  ACAAGAAATG  AGAGAAAATG  AGTTTAAGG   AGACTGTGCT  TAGCAAAGGC B. oleracea  TTGGAAAATC  TTGAGAGAGA  AGTTGAGGAT  GTTGATTGGG  AAAGCACTTT  CTACCTTCGT  AGTCCAATCT  CTACGACATT  CCTGATATGT
C. melo      TTAGAGGCTG  CACAAGCTGA  AGTTAATGAT  ATGGATTGGG  AAAGCACCTT  TTTCTTACGC  AATCAAACAT  CTCCCAGATG  TCTGATCTCG B. oleracea  CTGATGAATA  CCGGACGGCC  ATGAAAGATT  TTGGGAAGAG  ATTGGAGAAT  CTTGCTGAGG  ATTTGTTGGA  TCTATTGTGT  GGTTAGAGAA
C. melo      ACGAGGAGTA  TAAGAAAATT  ATGAAGGAAT  TTGCGAAGAA  ATTGGAGAAT  CTTGCTGAGG  AGTTGTTGGA  CCTGCTATGT  GGTTGGAGAA B. oleracea  AGGGTACTTG  AAGAAAGTTT  TTCATGGAAC  AAAAGGTCCA  ACCTTTGGGA  CTAAGGTGAG  GCTTGTCCTA  AGCCAGAGAT  GATCAAAGGT
C. melo      GGGTTATCTC  AAAAAGGCTT  TCTATGGTTC  AAAAAGGTCCT  ACATTTGGAA  CAAAGGTGAG  CCGTGTCCCA  AGCCGGACCT  CATCAAGGGT B. oleracea  CTTAGGGCCC  ACACTGATGC  AGGAGGCATC  ATCTTGTTGT  TTCAAGATGA  TTCCAGCAGC  GGTCTCCAGC  TTCCTAAAGA  TGGTGACTGG  ATTGATGTTC
C. melo      CTTCGAGCCC  ACACCGACGC  CGGTGCAGC   ATCCTCTCT   TCCAAGATGA  TCCAAGTAAGT  GGCCTGCCAAC  TCCTGAAAGA  TGGCAACTGG  ATCGACGTGC B. oleracea  CTCCACTCAA  CCACTCTATT  GTCATCAATC  TTGGTGACCA  ACTTGAGGTG  CCGGGAAGCG  GCAGGTACAA  GAGTGTGATG  CATCGTGTGG  TGACTCAGAA
C. melo      CCCCAATGCG  CCACGCCATT  GTCGTCAACC  TCGTGGACCA  ACTTGAGGTG  CCGGGGACGCG  GAAGATACAA  AAGTGTGATG  CATAGAGTGT  TAACTCAAAC B. oleracea  AGAAGGAAA.  .CAGAAATGT  CAATTGCATC  TTTCTACAAC  TTTGATGACT  ATGCTGAGAT  CTCTCCAGCT  TCATCGCTTG  CCTGTAAAGA  AACCGA....
C. melo      GAGTGGAACT  GGGCGAATGT  CGATAGCTTC  ATTCTACAAT  TTTGAAGATT  ACGCGGTGAT  CTACCCGGCG  CCGGCGCTAG  TGGAGAAAGA  TCAGGATGAG B. oleracea  ......GTACCC  AAGTTTTGTT  TTTGATGAGC  ACATGAAGCT  CTATGCTTGG  GTCAAGTTTC  AGCCTAAGGA  GCCACGGTTC  GAGGCAATGA
C. melo      GAGAAGAAGG  AAGTGTACCC  CAAGTTTGTG  TTTGAAGATT  ACATGAAGCT  GTATCTAGGA  GTGAAGTTTC  AGGCGAAGGA  GCCAAGATTT  GAAGCCATGA B. oleracea  AGAATGCTAA  TGCAGTTACA  GAATTG....A  ACCCAACAGC  ACTTTCTAAA  AACACCTAGG  AGTTTGAGCG
C. melo      AAGCCA....  .....ATGC.  .....T....A  ATTTGGGTCC  AATGGCAACA  GCCATAAT.TA  AACACCCAC  TTTTTCATTA  ATAGTAATAA  GGAATATTAG B. oleracea  .........  AGGGCTTGTG  TTTGCCCTTT  TTAAGTGGGT  CATCATTATT  GTTATTAAAT  GTCAAAACCA  AATATATAAA  TATACATATA  TATATATATG
C. melo B. oleracea  .........  TTTGGTAATT  GTAGCAACTT  AATAGGCTAA  AAGCTAGTAT  TTAGTGAAAA  CTCAATTTTC  TTTATAATTT  AAATTCACTT  TCAGCTTA..
C. melo B. oleracea  .........  .........
C. melo
```

TRANSGENIC PLANTS EXPRESSING ACC OXIDASE GENES

This application is a 371 of PCT/US95/07233 filed Jun. 7, 1995 which is a continuation-in-part of U.S. Ser. No. 08/300,335, filed on Sep. 2, 1994, now abandoned.

FIELD OF THE INVENTION

This invention relates to the plant enzyme ACC oxidase which is essential for the production of ethylene in higher plants. More particularly, the invention relates to the DNA sequence of a *Brassica oleracea* ACC oxidase, DNA constructs containing this sequence, plant cells containing the constructs and plants derived therefrom.

BACKGROUND OF THE INVENTION

The enzyme ACC oxidase (also known as ethylene forming enzyme) is essential to the production of ethylene in higher plants. It is well known that ethylene is related to various events in plant growth and development including fruit ripening, seed germination, abscission, and leaf and flower senescence. Ethylene production is strictly regulated by the plant and is induced by a variety of external factors, including the application of auxins, wounding, anaerobic conditions, viral infection, elicitor treatment, chilling, drought and ions such as cadmium and lithium ions, known as ethylene-inducible events. In addition, it recently has been shown that ethylene production begins after harvest (Tian et al. (1994) "A Role for Ethylene in the Yellowing of Broccoli After Harvest", *J. Amer. Soc. Hort. Sci.* Vol. 119: 276–281).

The pathway for ethylene synthesis in plants was first described by Adams and Yang, *PNAS, USA* 76:170–174 (1979) who identified 1-aminocyclopropane-1-carboxylic acid as an intermediate in the conversion of methionine to ethylene. The physiology and biochemistry of ethylene synthesis was extensively reviewed by Yang and Hoffman in *Ann. Rev. Plant Physiol.* 35:155–189 (1984).

In the ethylene biosynthetic pathway, methionine is catalyzed by the enzyme S-adenosylmethionine synthetase to form S-adenosylmethionine (SAM). SAM is then catalyzed to form the three-membered-ring amino acid 1-aminocyclopropane-1-carboxylic acid (ACC) by the enzyme ACC synthase. This three-membered-ring amino acid is then catalyzed by the enzyme ACC oxidase to form ethylene.

The ethylene forming enzyme genes in tomato plants were the first to be isolated. Smith et al. (1986) *Planta* 168:94–100 reported the rapid appearance of an mRNA correlated with ethylene synthesis encoding a protein of molecular weight 35000.

A number of molecular strategies have been used to inhibit ethylene formation in transgenic plants. Theologis et al., *Cell*, 70:181–184 (1992), report using updated antisense RNA and ACC deaminase approaches. Gray et al, *Plant Mol. Biol.* 19:69–87 (1992), report the manipulation of fruit ripening with antisense genes. Both ACC oxidase (Hamilton et al., *Nature* (1990) 346:284–296) and ACC synthase (Oeller et al, *Science* (1991) 254:437–439) antisense constructs have been used successfully to inhibit ethylene production in transgenic tomato plants. Klee et al. ((1991) *The Plant Cell* 3:1187–1193) overexpressed a Pseudomonas ACC deaminase gene in transgenic tomato plants. ACC deaminase converts ACC to a-ketobutyrate. This approach led to 90%–97% inhibition of ethylene production during fruit ripening in transgenic plants.

As is well known, a cell manufactures protein by transcribing the DNA of the gene for that protein to produce messenger RNA (mRNA), which is then processed (e.g., by the removal of introns) and finally translated by ribosomes into protein. This process may be inhibited by the presence in the cell of "antisense RNA". By this term is meant an RNA sequence which is complementary to a sequence of bases in the mRNA in question: complementary in the sense that each base (or the majority of bases) in the antisense sequence (read in the 3' to 5' sense) is capable of pairing with the corresponding base (G with C, A with U) in the mRNA sequence read in the 5' to 3' sense. It is believed that this inhibition takes place by formation of a complex between the two complementary strands of RNA, preventing the formation of protein. How this works is uncertain: the complex may interfere with further transcription, processing, transport or translation, or degrade the mRNA, or have more than one of these effects. Such antisense RNA may be produced in the cell by transformation with an appropriate DNA construct arranged to transcribe backwards part of the coding strand (as opposed to the template strand) of the relevant gene (or of a DNA sequence showing substantial homology therewith).

The use of this technology to downregulate the expression of specific plant genes is well known. Reduction of gene expression has led to a change in the phenotype of the plant: either at the level of gross visible phenotypic difference, e.g., lack of anthocyanin production in flower petals of petunia leading to colorless instead of colored petals (van der Krol et al., *Nature*, 333, 866–869, 1988); or at a more subtle biochemical level, e.g., change in the amount of polygalacturonase and reduction in depolymerization of pectin during tomato fruit ripening (Smith et al., *Nature*, 334, 724–726). Thus, antisense RNA has been proven to be useful in achieving downregulation of gene expression in plants.

INFORMATION DISCLOSURE

WO 92/04456 reports the isolation of a gene encoding the ACC synthase gene derived from zucchini and transgenic plants in which ethylene production is modified to control changes associated with fruit ripening.

WO 92/11371 reports a gene encoding an ethylene forming enzyme gene derived from melon and transgenic plants in which ethylene production is modified to control changes associated with fruit ripening, improved fruit quality, improved flavor and texture, and the possibility of production over a longer harvest period.

WO 92/11372 reports a peach gene encoding ethylene forming enzyme and plants transformed with the peach ethylene forming enzyme gene construct. These constructs modify ethylene-associated ripening changes, reduced rate of deterioration after harvest, and allowed storage for longer periods.

WO 94/08449 reports the isolation of a gene encoding the ACC synthase polypeptide derived from Crucifer and transgenic plants in which ethylene production is modified to control changes associated with fruit ripening.

Balague et al., (1993) *Eur. J. Biochem.* 212:27–34 reported the isolation and sequencing of an ethylene forming gene from melon (*Cucumis melo L.*) where the predicted amino acid sequence of the melon ACC oxidase gene appears to be closely related to the sequences reported for 3 tomato ACC oxidase genes (81%, 81% and 77% identity), an avocado ACC oxidase gene (73% identity), and a carnation ACC oxidase gene (75% identity). The authors speculate that transforming melon with pMEL1 antisense transgene should allow them to determine whether ethylene biosynthesis can be inhibited in ripening melon and whether this inhibition will delay ripening processes. However, the engineering of constructs for plant transformation or expression was not reported.

Gray et al., *Plant Mol. Biol.* 19:69–87 (1992) report the molecular biology of fruit ripening and its manipulation with antisense genes.

Hamilton et al. (1990) *Nature* 346:284–286 report the transformation of chimeric pTOM13 antisense gene construct into the tomato variety Ailsa Craig. All transformants showed reduced ethylene biosynthesis. Ethylene production in wounded leaves of primary transformants was inhibited by 68% and by 87% in ripening fruit.

Holdsworth et al. (1987) *Nucl. Acids Res.* 15:731–739 report the structure and expression of an ethylene-related mRNA from tomato.

Holdsworth et al. (1987) *Nuc. Acids Res.* 15:10600 report the isolation and sequencing of a genomic clone (GTOMA) of tomato ethylene forming enzyme. Transgenic tomato plants expressing antisense RNA to tomato ethylene forming enzyme sequences displayed reduced ethylene synthesis.

Kende (1993) *Ann. Rev. Plant Physiol. Plant Mol. Biol.* 44:283–307 reports a history of the study of the ethylene biosynthetic pathway.

Kim, W. T. and Yang, S. F. (1993) *Plant Physiol. Suppl.* 102:26 reported the isolation and characterization of cDNAs encoding 1-aminocyclopropane-1-carboxylate oxidase homologs from mung bean hypocotyls.

Klee et al. ((1991) *The Plant Cell* 3:1187–1193) reports the overexpression of a Pseudomonas ACC deaminase gene in transgenic tomato plants to inhibit ethylene production during fruit ripening.

McGarvey et al. (1990) *Plant Mol. Biol.* 15:165–167 report the nucleotide sequence of a ripening-related cDNA from avocado fruit.

Oeller et al. (1991) *Science* 254:437–439 report the reversible inhibition of tomato fruit senescence by antisense ACC synthase RNA.

Pua et al. (1992) *Plant Mol. Biology* 19:541–544, report the isolation and sequence analysis of a cDNA clone encoding ethylene-forming enzyme in *Brassica juncea* but did not report any genomic clone or genetic sequence and reported no engineering for plant expression or plant transformation.

Smith et al. (1986) *Planta* 168:94–100 reported the rapid appearance of an mRNA correlated with ethylene synthesis encoding a protein of molecular weight 35000.

Theologis, *Cell* 70:181–184 (1992) report using updated antisense RNA and ACC deaminase approaches to control fruit ripening.

Theologis et al. (1993) *Dev. Genet.* 14:282–295 report the reversible inhibition of tomato fruit senescence by antisense ACC synthase RNA.

Theologis et al. (1992) *Plant Physiol.* 100:549–551 report the modification of fruit ripening by suppressing gene expression.

Tian et al. (1994) *J. Amer. Soc. Hort. Sci.* Vol. 119:276–281 reports ethylene production and the yellowing of broccoli begins after harvest.

Wang et al. (1991) *Plant Physiol.* 96:1000–1001 isolated the ACC oxidase cDNA sequenced of a carnation (*Dianthus caryophyllus*) by screening a cDNA library with the tomato efe gene pTOM13 and an avocado efe gene pAVOe3.

Wang et al. (1992) *Plant Physiol.* 100:535–536 isolated the ACC oxidase cDNA sequence of *Petunia corollas*.

Yang (1984) *Ann. Rev. Plant Physiol.* 35:155–189 report generally on ethylene biosynthesis and its regulation in higher plants.

SUMMARY OF THE INVENTION

The present invention provides recombinant materials which permit control of the level of ACC oxidase in plants, specifically, *Brassica oleracea* and *Cucumis melo*. The invention is also directed to DNA in purified and isolated form comprising a DNA sequence encoding the enzyme ACC oxidase of *Brassica oleracea* and *Cucumis melo*. The invention is also directed to expression systems effective in expressing the DNA encoding said ACC oxidase and to recombinant hosts transformed with this expression system. The invention is further directed to methods to control ACC oxidase production and, thus, the growth and development of *Brassica oleracea* and *Cucumis melo* plants, using the coding sequences for ACC oxidase in an antisense construct or by replacing the ACC oxidase gene by a mutated form thereof. The invention thus provides a method for controlling the maturation and aging of *Brassica oleracea* and *Cucumis melo* plants which allows one to influence, e.g., lengthen, the shelflife of these plants.

BRIEF DESCRIPTION OF THE FIGURES

FIG. 1 illustrates the amino acid sequence of *B. oleracea* ACC oxidase [SEQ ID NO:1], the cDNA sequence of *B. oleracea* ACC oxidase [SEQ ID NO:2] and the restriction enzyme cloning sites for PCR oligomer reaction primers;

FIG. 2 illustrates the cDNA and amino acid sequences of *B. oleracea* ACC oxidase [SEQ ID NOS:1 and 2] compared to the cDNA and amino acid sequences of *B. juncea* ACC oxidase [SEQ ID NOS:9 and 10];

FIG. 3 illustrates the PCR oligomer reaction primers and the novel restriction enzyme cloning sites for each of the primers used for the amplification of the DNA nucleotide sequence of the *B. oleracea* ACC oxidase gene [SEQ ID NO:8] from the portion of the *B. oleracea* genome containing the DNA sequence of the *B. oleracea* ACC oxidase and compares to the genomic DNA sequence with the cDNA sequence of *B. oleracea* ACC oxidase;

FIG. 9 illustrates a comparison of melon ACC oxidase nucleotide sequence [SEQ ID NO:14] with *B. oleracea* nucleotide sequence [SEQ ID NO:13]. Sequences were aligned with the use of the Pileup Program in the UWGCG program package.

DETAILED DESCRIPTION OF THE PREFERRED EMBODIMENT

Figure 4A:
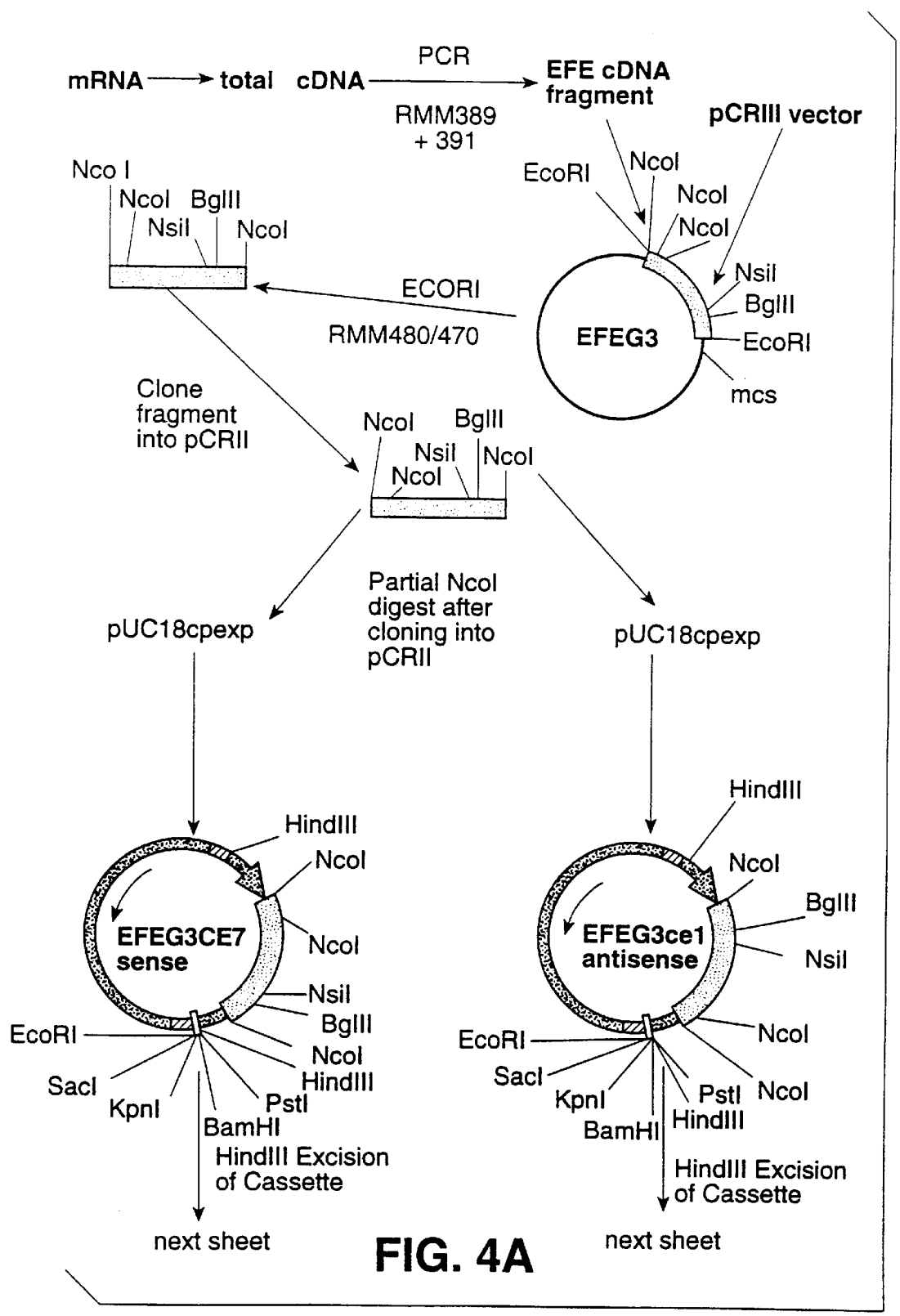
FIG. 4 illustrates a flow chart showing the engineering steps used to install the ACC oxidase cDNA coding sequence, both in the sense and the antisense orientation, into plant expression vectors and the subsequent insertion into binary plasmids.

Most of the recombinant DNA methods employed in practicing the present invention are standard procedures, well known to those skilled in the art. Enzymes are obtained from commercial sources and are used according to the vendor's recommendations or other variations known to the art. Reagents, buffers, and culture conditions are also known to those in the art. General references containing such standard techniques include the following: R. Wu, ed. (1979) *Methods in Enzymology,* Vol. 68; J. H. Miller (1972) *Experiments in Molecular Genetics;* D. M. Glover, ed. (1985) *DNA Cloning,* Vol. II; S. B. Gelvin and R. A. Schilperoort, eds. *Introduction, Expression, and Analysis of Gene Products in Plants;* and Sambrook et al., *Molecular Cloning: A Laboratory Manual,* Second Edition (1989) Cold Spring Harbor Laboratory Press, Cold Spring Harbor all of which are incorporated by reference.

As used herein, "recombinant" refers to a nucleic acid sequence which has been obtained by manipulation of genetic material using restriction enzymes, ligases, and similar recombinant techniques as described by, for example, Sambrook et al., *Molecular Cloning: A Laboratory Manual,* Second Edition (1989) Cold Spring Harbor Laboratory Press, Cold Spring Harbor. "Recombinant", as used herein, does not refer to naturally-occurring genetic recombinations.

As defined herein, "ACC oxidase" includes enzymes which are capable of catalyzing the conversion of ACC to ethylene. The amino acid sequence of the oxidase may or may not be identical with the amino acid sequence which occurs natively in higher plants. An example of such a native sequence is shown in FIG. 1 [SEQ ID NO:1] which occurs in broccoli. Naturally occurring allelic variants undoubtedly occur as well. In addition, artificially induced mutations are also included so long as they do not destroy activity. In general, conservative amino acid substitutions can be made for most of the amino acids in the primary structure as shown without effecting destruction of activity. Thus, the definition of ACC oxidase used herein includes those variants which are derived by direct or indirect manipulation of the disclosed sequence.

It is also understood that the primary structure may be altered by post-translational processing or by subsequent chemical manipulation to result in a derivatized protein which contains, for example, glycosylation substituents, oxidized forms of, for example, cysteine or proline, conjugation to additional moieties, such as carriers, solid supports, and the like. These alterations do not remove the protein from the definition of ACC oxidase so long as its capacity to convert ACC to ethylene is maintained.

Thus, the identity of an enzyme as "ACC oxidase" can be confirmed by its ability to effect the production of ethylene in an assay performed as follows: 5 ng to 0.5 mg of enzyme protein in a 500-uL volume is added to 2.5 mL of assay buffer [50 mM Tris-HCl (pH 7.2), 10% (v/v) glycerol, 0.1 mM $FeSO_4$, 10 mM ascorbate, 1 mM ACC, and 1 mM 2-oxoglutarate] in 25-mL Erlenmeyer flasks. The vials are sealed with serum caps and incubated for 1 hr at 23° C. shaking gently. Air in the headspace is analyzed by gas chromatography on a Varian 3400 gas chromatograph equipped with a flame ionization detector and an 80% Porapak N/20% Porapak Q column. Ethylene production is quantitated by comparison with a 97.7 ppm ethylene gas mixture in helium (Alltech Associates). A unit is defined as 1 nL/hr. Pirrung et al. (1993) *Biochemistry* 32:7445–7450, teach the purification and properties of the apple fruit ethylene-forming enzyme. While alternative forms of assessment of ACC oxidase can be devised, and variations on the above protocol are certainly permissible, the foregoing provides a definite criterion for the presence of ACC oxidase activity and classification of a test protein as ACC oxidase.

The amino acid sequence for ACC oxidase in broccoli is shown in FIG. 1 [SEQ ID NO:1]. Preferred forms of the ACC oxidase of the invention include that illustrated herein, and those derivable therefrom by systematic mutation of the genes. Such systematic mutation may be desirable to enhance the ACC oxidase properties of the enzyme, to enhance the characteristics of the enzyme which are ancillary to its activity, such as stability, or shelf life, or may be desirable to provide inactive forms useful in the control of ACC oxidase activity in vivo.

As described above, "ACC oxidase" refers to a protein having the activity assessed by the assay set forth above; a "mutated ACC oxidase" refers to a protein which does not necessarily have this activity, but which is derived by mutation of a DNA encoding in ACC oxidase. By "derived from mutation" is meant both direct physical derivation from a DNA encoding the starting material ACC oxidase using, for example, site specific mutagenesis or indirect derivation by synthesis of DNA having a sequence related to, but deliberately different from, that of the ACC oxidase. As means for constructing oligonucleotides of the required length are available, such DNAs can be constructed wholly or partially from their individual constituent nucleotides.

INITIAL ISOLATION OF THE ACC OXIDASE cDNA

In view of the recent studies which have shown that ethylene production begins after harvest (Tian et al. (1994) *J. Amer. Soc. Hort. Sci.* Vol. 119:276–281), one does not have to wait until a plant illustrates visible signs of senescence to ensure one harvests the mRNA needed for ethylene production. After isolating total mRNA from plants such as *Brassica oleracea* var. *Italica* or *Cucumis melo* by methods well known in the art, such as single step liquid-phase separation, the mRNA is purified. The mRNA is then treated with reverse transcriptase to produce total first strand cDNA.

Polymerase chain reaction (PCR) primers can then be used to amplify the ACC oxidase gene from the cDNA template. In the case of *Brassica oleracea* and *Cucumis melo,* because it was suspected that its ACC oxidase DNA sequence would be similar to the ACC oxidase cDNA sequence of other species, oligonucleotides used to prime the PCR were modeled after sequences of a cDNA clone of the ACC oxidase gene found in *Brassica juncea* (Pua et al. (1992) *Plant Mol. Biology* 19:541–544).

With the ACC oxidase gene available because of PCR amplification, ACC oxidase can be produced in a variety of recombinant systems. Specifically, the ACC oxidase can be expressed in transgenic plants both in enhanced amounts and in an antisense mode to control the aspects of plant development which are ethylene sensitive, and in particular, to delay plant senescence.

Accordingly, a variety of expression systems and hosts can be used for the production of this enzyme. A variety of prokaryotic hosts and appropriate vectors is known in the art; most commonly used are *E. coli* or other bacterial hosts such as *B. subtilis* or Pseudomonas and typical bacterial promoters include the trp, lac, tac, and beta-lactamase promoters. A readily controllable, inducible promoter, the lambda-phage promoter can also be used. A large number of control systems suitable for prokaryote expression is known in the art.

Similarly, a large number of recombinant systems have been developed for expression in eukaryotic hosts, including yeasts, insect cells, mammalian cells, and plant cells. These systems are well characterized and require the ligation of the coding sequence under the control of a suitable transcription initiating system (promoter) and, if desired, termination sequences and enhancers. Especially useful in connection with the ACC oxidase gene of the present invention are expression systems which are operable in plants. These include systems which are under control of a tissue-specific promoter, as well as those which involve promoters that are operable in all plant tissues.

Transcription initiation regions, for example, include the various opine initiation regions, such as ocotopine, mannopine, nopaline and the like. Plant viral promoters can also be used, such as the cauliflower mosaic virus 35S promoter. In addition, plant promoters such as ribulose-1,3-diphosphate carboxylase, flower organ-specific promoters, heat shock promoters, seed-specific promoters, promoters that are transcriptionally active in associated vegetable tissue. etc. can also be used.

The cauliflower mosaic virus (CaMV) 35S promoter has been shown to be highly active in many plant organs and during many stages of development when integrated into the genome of transgenic plants including tobacco and petunia, and has been shown to confer expression in protoplasts of both dicots and monocots.

The CaMV 35S promoter has been demonstrated to be active and may be used in at least the following monocot and dicot plants with edible parts: blackberry, Rubus; blackberry/raspberry hybrid, Rubus, and red raspberry; carrot, *Daucus carota;* maize; potato, *Solanum tuberosum;* rice, *Oryza sativa;* strawberry, *Fragaria x ananassa;* and tomato, *Lycopersicon esculentum.*

The nopaline synthase (Nos) promoter has been shown to be active and may be used in at least the following monocot and dicot plants with edible parts: apple, *Malus pumila;* cauliflower, *Brassica oleracea;* celery, *Apium graveolens;* cucumber, *Cucumis sativus;* eggplant, *Solanum melongena;* lettuce, *Lactuca sativa;* potato, *Solanum tuberosum;* rye, *Secale cereale;* strawberry, *Fragaria x ananassa;* tomato, *Lycopersicon esculentum;* and walnut, *Juglans regia.*

Organ-specific promoters are also well known. For example, the E8 promoter is only transcriptionally activated during tomato fruit ripening, and can be used to target gene expression in ripening tomato fruit (Deikman and Fischer, *EMBO J* (1988) 7:3315). The activity of the E8 promoter is not limited to tomato fruit, but is thought to be compatible with any system wherein ethylene activates biological processes. Other organ-specific promoters appropriate for a desired target organ can be isolated using known procedures. These control sequences are generally associated with genes uniquely expressed in the desired organ. In a typical higher plant, each organ has thousands of mRNAs that are absent from other organ systems (reviewed in Goldberg, *Trans., R. Soc. London* (1986) B314:343).

To create an expression system, the gene coding for ACC oxidase in hand is ligated to a promoter using standard techniques now common in the art. The expression system may be further optimized by employing supplemental elements such as transcription terminators and/or enhancer elements.

Thus, for expression in plants, the recombinant expression cassette will contain in addition to the ACC oxidase-encoding sequence, a plant promoter region, a transcription initiation site (if the coding sequence to be transcribed lacks one), and a transcription termination sequence. Unique restriction enzyme sites at the 5' and 3' ends of the cassette are typically included to allow for easy insertion into a pre-existing vector.

Sequences controlling eukaryotic gene expression have been extensively studied. Promoter sequence elements include the TATA box consensus sequence (TATAAT), which is usually 20–30 base pairs (bp) upstream of the transcription start site. In most instances, the TATA box is required for accurate transcription initiation. By convention, the start site is called +1. Sequences extending in the 5' (upstream) direction are given negative numbers and sequences extending in the 3' (downstream) direction are given positive numbers.

In plants, further upstream from the TATA box, at positions −80 to −100, there is typically a promoter element with a series of adenines surrounding the trinucleotide G (or T)NG (Messing, J. et al., in *Genetic Engineering in Plants,* Kosage, Meredith and Hollaender, eds. (1983) pp. 221–227). Other sequences conferring tissue specificity, response to environmental signals, or maximum efficiency of transcription may also be found in the promoter region. Such sequences are often found within 400 bp of transcription initiation site, but may extend as far as 2000 bp or more.

In the construction of heterologous promoter/structural gene combinations, the promoter is preferably positioned about the same distance from the heterologous transcription start site as it is from the transcription start site in this natural setting. As is known in the art, however, some variation in this distance can be accommodated without loss of promoter function.

As stated above, any of a number of promoters which direct transcription in plant cells is suitable. The promoter can be either constitutive or inducible. Promoters of bacterial origin include the octopine synthase promoter, the nopaline synthase promoter and other promoters derived from native Ti plasmids (Herrera-Estrella et al., *Nature* (1983) 303:209–213). Viral promoters include the 35S and 19S RNA promoters of cauliflower mosaic virus (O'Dell et al., *Nature* (1985) 313:810–812. Plant promoters include the ribulose-1,3-diphosphate carboxylase small subunit promoter and the phaseolin promoter.

In addition to a promoter sequence, the expression cassette should also contain a transcription termination region downstream of the structural gene to provide for efficient termination. The termination region may be obtained from the same gene as the promoter sequence or may be obtained from different genes.

If the mRNA encoded by the structural gene is to be efficiently processed, DNA sequences which direct polyadenylation of the RNA are also commonly added to the vector construct (Albert and Kawaski, *Mol. and Appl. Genet.* (1982) 1:419–434). Polyadenylation is of importance for expression of the ACC oxidase-encoding RNA in plant cells. Polyadenylation sequences include, but are not limited to the Agrobacterium octopine synthase signal (Gielen et al., *EMBO J* (1984) 3:835–846) or the nopaline synthase signal (Depicker et al., *Mol. and Appl. Genet.* (1982) 1:561–573).

The resulting expression system or cassette is ligated into or otherwise constructed to be included in a recombinant vector which is appropriate for higher plant transformation. The vector will also typically contain a selectable marker gene by which transformed plant cells can be selected for and identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow on a medium containing the particular antibiotic. Replication sequences, of bacterial or viral origin, are generally also included to allow the vector to be cloned in a bacterial or phage host, preferably a broad host range prokaryotic origin of replication is included. A selectable marker for bacteria should also be included to allow selection of bacterial cells bearing the desired construct. Suitable prokaryotic selectable markers also include resistance to antibiotics such as kanamycin or tetracycline.

Other DNA sequences encoding additional functions may also be present in the vector, as is known in the art. For instance, in the case of Agrobacterium transformation, T-DNA sequences will also be included for subsequent transfer to plant chromosomes.

In addition, vectors can also be constructed that contain in-frame ligations between the sequence encoding the ACC oxidase protein and sequences encoding other molecules of interest resulting in fusion proteins, by techniques well known in the art.

When an appropriate vector is obtained, transgenic plants are prepared which contain the desired expression system. A number of techniques are available for transformation; in general, only dicots can be transformed using Agrobacterium-mediated infection.

In one form of direct transformation, the vector is microinjected directly into plant cells by use of micropippettes to mechanically transfer the recombinant DNA (Crossway, *Mol. Gen. Genetics* (1985) 202:179–185). In another form, the genetic material is transferred into the plant cell using polyethylene glycol (Krens, et al. *Nature* (1982) 296:72–74), or high velocity ballistic penetration by small particles with the nucleic acid either within the matrix of small beads or particles, or on the surface, is used (Klein, et al., *Nature* (1987) 327:70–73). In still another method protoplasts are fused with other entities which contain the DNA whose introduction is desired. These entities are minicells, cells, lysosomes or other fusible lipid-surfaced bodies (Fraley, et al., *Proc. Natl. Acad. Sci. USA* (1982) 79:1859–1863.

DNA may also be introduced into the plant cells by electroporation (Fromm et al., *Proc. Natl. Acad. Sci. USA* (1985) 82:5824). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide and regenerate.

For transformation mediated by bacterial infection, a plant cell is infected with *Agrobacterium tumefaciens* or *Agrobacterium rhizogenes* previously transformed with the DNA to be introduced. Agrobacterium is a representative genus of the gram-negative family Rhizobiaceae. Its species are responsible for crown gall (*A. tumefaciens*) and hair root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by Agrobacterium and is stably integrated into the plant genome (Schell, J., *Science* (1987) 237:1176–1183). Ti and Ri plasmids contain two regions essential for the production of transformed cells. One of these, named transferred DNA (T-DNA), is transferred to plant nuclei and induces tumor or root formation. The other, termed the virulence (vir) region, is essential for the transfer of the T-DNA but is not itself transferred. The T-DNA will be transferred into a plant cell even if the vir region is on a different plasmid (Hoekema, et al., *Nature* (1983) 303:179–189). The transferred DNA region can be increased in size by the insertion of heterologous DNA without its ability to be transferred being affected. Thus a modified Ti or Ri plasmid, in which the disease-causing genes have been deleted, can be used as a vector for the transfer of the gene constructs of this invention into an appropriate plant cell.

Construction of recombinant Ti and Ri plasmids in general follows a method typically used with the more common bacterial vectors, such as pBR322. Additional use can be made of accessory genetic elements sometimes found with the native plasmids and sometimes constructed from foreign sequences. These may include but are not limited to "shuttle vectors", (Ruvkum and Ausubel, *Nature* (1981) 298:85–88), promoters (Lawton et al., *Plant Mol. Biol.* (1987) 9:315–324) and structural genes for antibiotic resistance as a selection factor (Fraley et al., *Proc. Natl. Acad. Sci.* (1983) 80:4803–4807).

There are two classes of recombinant Ti and Ri plasmid vector system now in use. In one class, called "cointegrate," the shuttle vector containing the gene of interest is inserted by genetic recombination into a non-oncogenic Ti plasmid that contains both the cis-acting and trans-acting elements required for plant transformation as, for example, in the PMLJ1 shuttle vector of DeBlock et al., *EMBO J* (1984) 3:1681–1689 and the non-oncogenic Ti plasmid pGV2850 described by Zambryski et al., *EMBO J* (1983) 2:2143–2150. In the second class or "binary" system, the gene of interest is inserted into a shuttle vector containing the cis-acting elements required for plant transformation. The other necessary functions are provided in trans by the non-oncogenic Ti plasmid as exemplified by the pBIN19 shuttle vector described by Bevan, *Nucleic Acids Research* (1984) 12:8711–8721 and the non-oncogenic Ti plasmid PAL4404 described by Hoekma, et al., *Nature* (1983) 303:179–180. Some of these vectors are commercially available.

There are two common ways to transform plant cells with Agrobacterium: co-cultivation of Agrobacterium with cultured isolated protoplasts, or transformation of intact cells or tissues with Agrobacterium. The first requires an established culture system that allows for culturing protoplasts and subsequent plant regeneration from cultured protoplasts. The second method requires (a) that the intact plant tissues, such as cotyledons, can be transformed by Agrobacterium and (b) that the transformed cells or tissues can be induced to regenerate into whole plants.

Most dicot species can be transformed by Agrobacterium as well as species which are a natural plant host for Agrobacterium are transformable in vitro. Monocotyledonous plants, and in particular, cereals, are not natural hosts to Agrobacterium. Attempts to transform them using Agrobacterium have been unsuccessful until recently (Hooykas-Van Slogteren et al., *Nature* (1984) 311:763–764). However, there is growing evidence now that certain monocots can be transformed by Agrobacterium. Using novel experimental approaches cereal species such as rye (de la Pena et al., Nature (1987) 325:274–276), maize (Rhodes et al., *Science* (1988) 240:204–207), and rice (Shimamoto et al., *Nature* (1989) 338:274–276) may now be transformed.

Identification of transformed cells or plants is generally accomplished by including a selectable marker in the transforming vector, or by obtaining evidence of successful bacterial infection.

Plant cells which have been transformed can also be regenerated using known techniques.

Plant regeneration from cultured protoplasts is described in Evans et al., *Handbook of Plant Cell Cultures*, Vol. 1: (MacMilan Publishing Co. New York, 1983); and Vasil I. R. (ed.), *Cell Culture and Somatic Cell Genetics of Plants*, Acad. Press, Orlando, Vol. I, 1984, and Vol. II, 1986). It is known that practically all plants can be regenerated from cultured cells or tissues, including but not limited to, all major species of sugar-cane, sugar beet, cotton, fruit trees, and legumes.

Means for regeneration vary from species to species of plants, but generally a suspension of transformed protoplasts or a petri plate containing transformed explants is first provided. Callus tissue is formed and shoots may be induced from callus and subsequently root. Alternatively, somatic embryo formation can be induced in the callus tissue. These somatic embryos germinate as natural embryos to form plants. The culture media will generally contain various amino acids and plant hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

A large number of plants have been shown capable of regeneration from transformed individual cells to obtain transgenic whole plants. For example, regeneration has been shown for dicots as follows: apple, *Malus pumila;* blackberry, Rubus; Blackberry/raspberry hybrid, Rubus; red raspberry, Rubus; carrot, *Daucus carota,* cauliflower, *Brassica oleracea;* celery, *Apium graveolens;* cucumber, *Cucumis sativus;* eggplant, *solanum melongena;* lettuce, *Lactuca sativa;* potato, *Solanum tuberosum;* rape, *Brassica napus;* soybean (wild), *Glycine Canescens;* strawberry, *Fragaria x ananassa;* tomato, *Lycopersicon esculentum;* walnut, *Juglans regia;* melon, *Cucumis melo;* grape, *Vitis vinifera;* mango, *Mangifera indica;* and for the following monocots; rice, *Oryza sativa;* rye, *Secale cereale;* and maize.

In addition, regeneration of whole plants from cells (not necessarily transformed) has been observed in: apricot, *Prunus armeniaca;* asparagus, *Asparagus officinalis;* banana, hydrib Musa; bean, *Phaseolus vulgaris;* cherry, hybrid Prunus; grape, *Vitis vinifera;* mango, *Mangifera indica;* melon, *Cucumis melo;* ochra, *Abelmoschus esculentus;* onion, hybrid Allium; orange, *Citrus sinensis;* papaya, *Carrica papaya;* peach, *Prunus persica* and plum, *Prunus domestica;* pear, *Pyrus communis;* pineapple, *Ananas comosus;* watermelon, *Citrullus vulgaris;* and wheat, *Triticum aestivum.*

The regenerated plants selected from those listed are transferred to standard soil conditions and cultivated in a conventional manner.

After the expression cassette is stably incorporated into regenerated transgenic plants, it can be transferred to other plants by sexual crossing. Any of a number of standard breeding techniques can be used, depending upon the species to be crossed.

The plants are grown and harvested using conventional procedures.

ACC OXIDASE GENE OBTAINED FROM *B. OLERACEA* cDNA CLONES

EXAMPLE 1

Isolation of Total RNA from Broccoli Beads (Florets)

Total RNA was isolated from broccoli florets (beads) by use of TRI-REAGENT RNA/DNA/protein isolation reagent (a single step liquid-phase separation) (Molecular Research Center, Inc., Cincinnati, Ohio). The instructions provided with the reagent were followed to accomplish the isolation.

EXAMPLE 2

Enrichment for polyA$^+$ RNA

Oligo dT-cellulose chromatography was then used to enrich for polyA$^+$ RNA. The procedure involved mixing total broccoli floret RNA (this includes messenger RNA or polyA$^+$ RNA) with oligo dT-cellulose in 20 mM NaCl and Tris buffer. The oligo-dT cellulose was washed to eliminate non-polyadenylated RNAs from the cellulose. Subsequently, polyA$^+$ RNA was eluted from the cellulose by elution in Tris buffer that includes no NaCl. Sambrook et al. (1989) "Selection of poly(A)$^+$ RNA", *Molecular Cloning: A Laboratory Manual,* Second Edition, pp. 7.26–7.29.

EXAMPLE 3

Synthesis of Single-stranded cDNA

Single-stranded cDNA was synthesized using the polyA$^+$ RNA template from Example 2. A 50 uL reaction included 1× First Strand cDNA Synthesis Buffer (GIBCO BRL, Gaithersburg, Md.), 1 ug polyA$^+$ RNA, 1 mM dNTP's (USB, Cleveland Ohio), 1 ug oligo dT, 1 uL RNasin (Promega, Madison, Wis.), 3.3 uM dithiothreitol, 5 uL $^{32}$PdCTP (3000 Ci/mmol, NENDuPont NEG013H, Wilmington, Del.), and 1 uL RTase Superscript (GIBCO BRL, Gaithersburg, Md.). Single-stranded *B. oleracea* cDNA was purified by the use of columns (Qiaquick-spin PCR column) obtained from Qiagen (Chatsworth, Calif.). First strand cDNA was characterized by hydroxide agarose gel electrophoresis; based on electrophoretic mobility, the size distribution of first strand cDNA was estimated to center near 1 kilobase.

EXAMPLE 4

PCR Amplification of Target cDNA ACC Oxidase Sequences

An ACC oxidase cDNA sequence was PCR amplified from total *Brassica oleracea* first strand cDNA with the use of the cDNA template obtained as above. The polymerase chain reaction (PCR) was carried out using reagents supplied with the Perkin Elmer Cetus Gene Amp PCR Kit under the following conditions: ~0.1 ug/mL total cDNA of *Brassica oleracea,* 1.5 mM MgCl$_2$, 24 ug/mL of each oligomer primer, 200 uM each dNPT, kit reaction buffer, and Ampli-Taq DNA ploymerase supplied with the kit. Reaction tubes were subjected to 93° C. for 1 min, 55° C. for 1 min, the 72° C. for 3 min for 30 cycles in a Perkin Elmer Thermocycler. Oligonucleotides used to prime the PCR were modeled after sequences of a cDNA clone of the ACC oxidase gene found in *brassica juncea* (Pua et al. (1992) *Plant Mol. Biology* 19:541–544). Oligomer primers RMM389 (5' GAGAGAGCCATGGAGAAGAACATTAAGTTTCCAG 3', complementary to the 5' end of the cDNA clone of *brassica juncea* ACC oxidase gene) (SEQ ID NO:3) and RMM391 (5' CGGCATCTCTGAAAGATTTTTGTG-GATCCTCAAACTCGC 3', complementary to the 3' end of the cDNA clone of *Brassica juncea* ACC oxidase gene) (SEQ ID NO:4) were used to prime this reaction. FIG. 2 illustrates the cDNA and amino acid sequences of *B. oleracea* ACC oxidase [SEQ ID NOS:1 and 2] compared to the cDNA and amino acid sequences of *B. juncea* ACC oxidase [SEQ ID NOS:9 and 10].

EXAMPLE 5

Cloning an ACC Oxidase PCR Fragment into the pCRII Vector

Figure 4B:
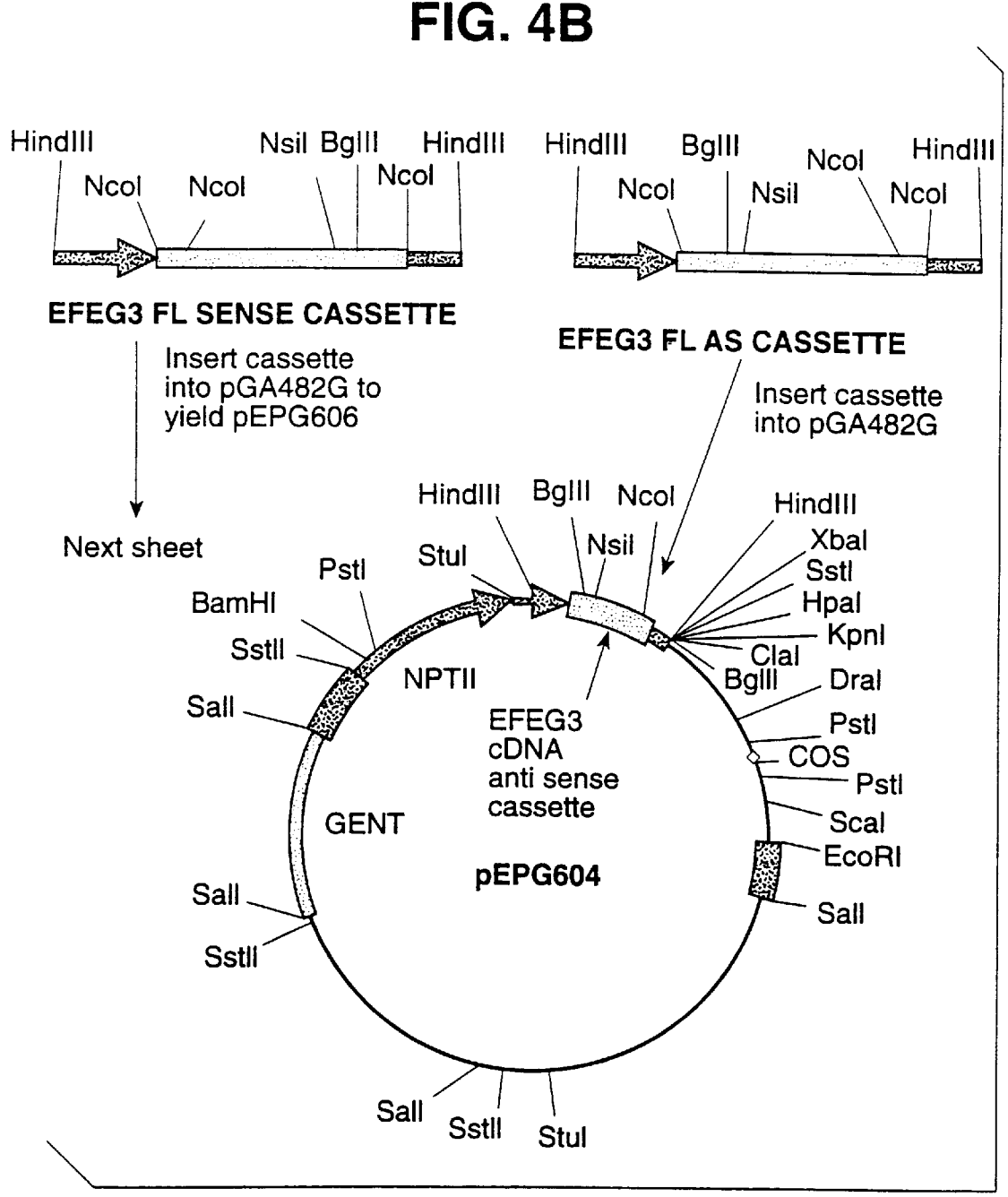
Figure 4C:
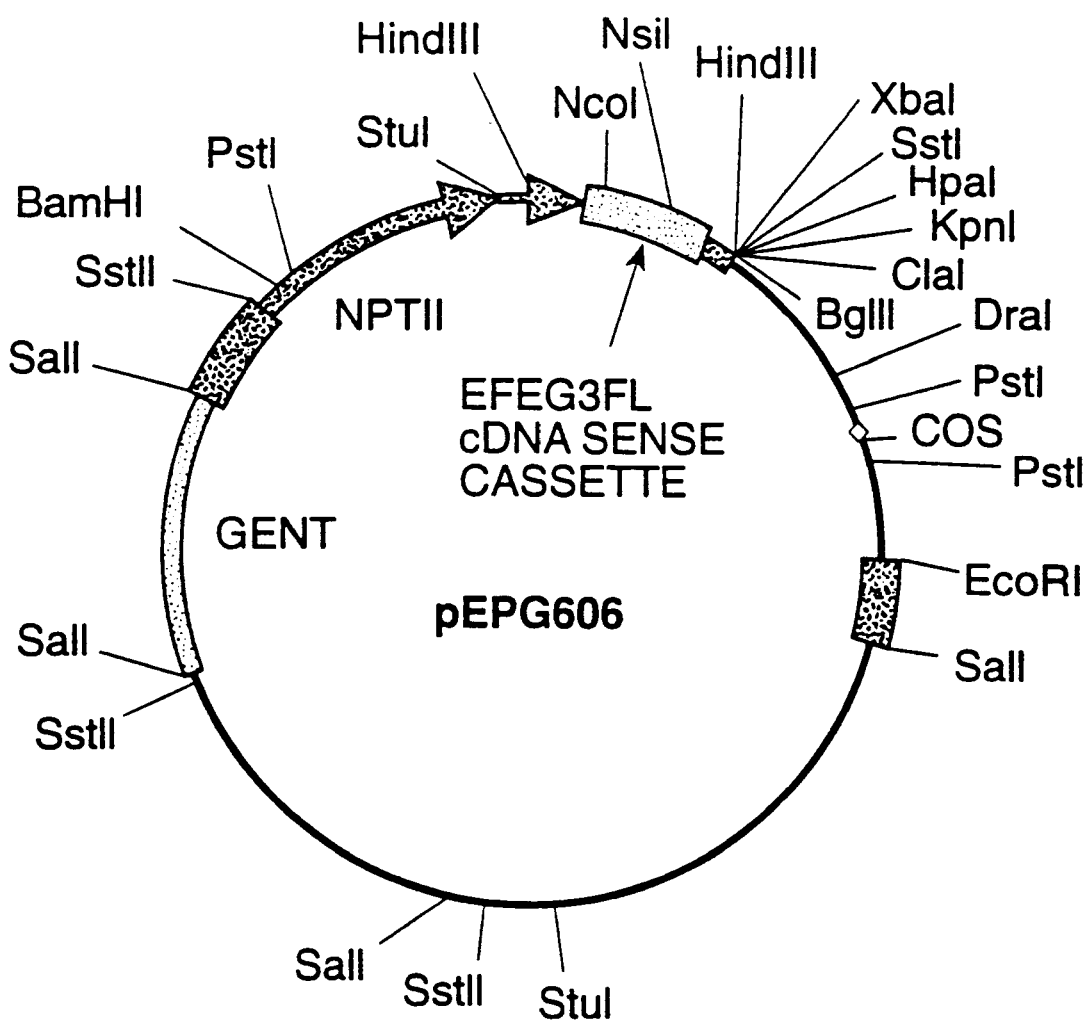
Figure 5A:
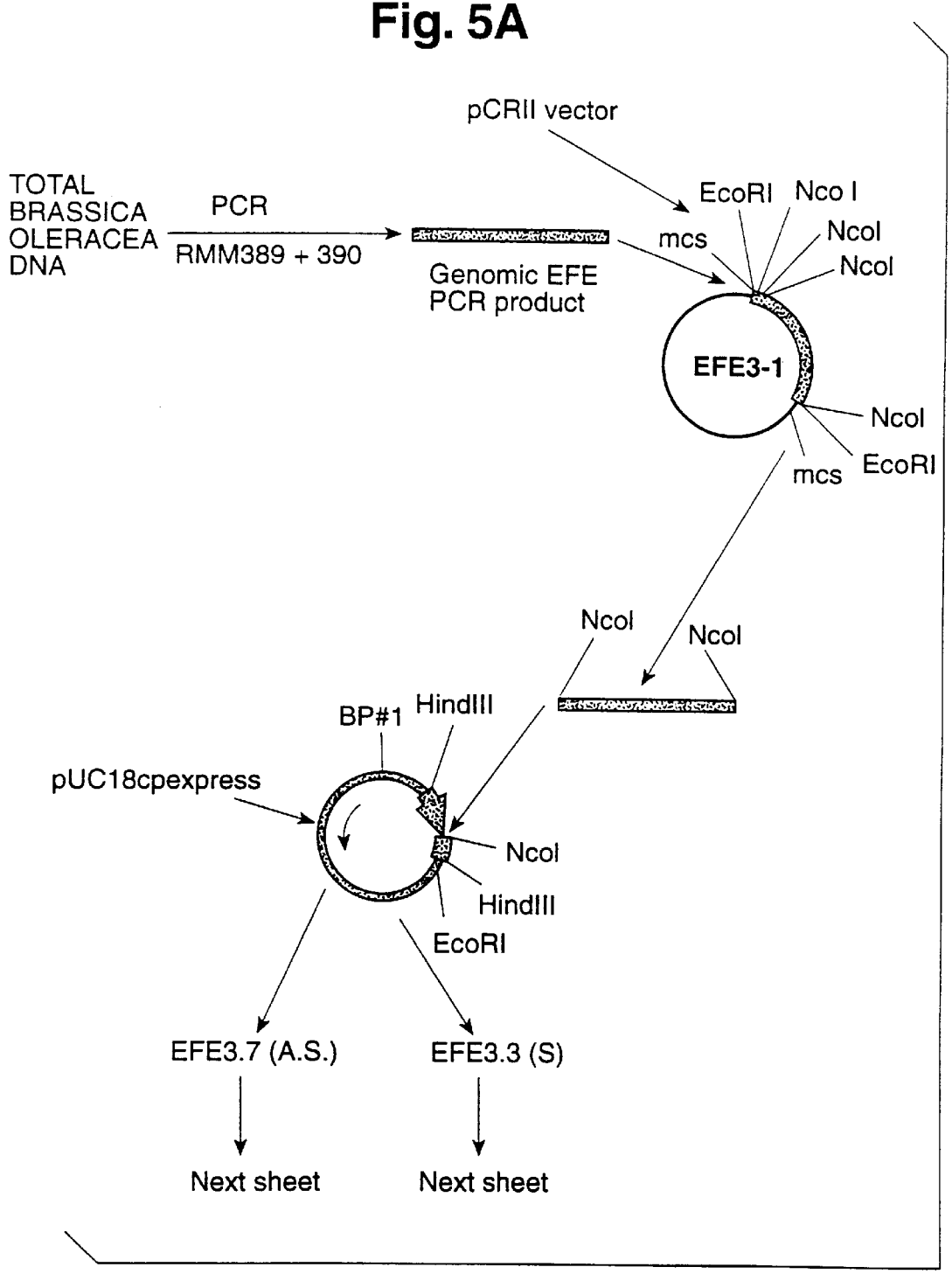
FIG. 5 illustrates a flow chart showing the engineering steps used to install the *B. oleracea* ACC oxidase genomic DNA coding sequence, both in the sense and the antisense orientation, into plant expression vectors and the subsequent insertion into binary plasmids.
Figure 5B:
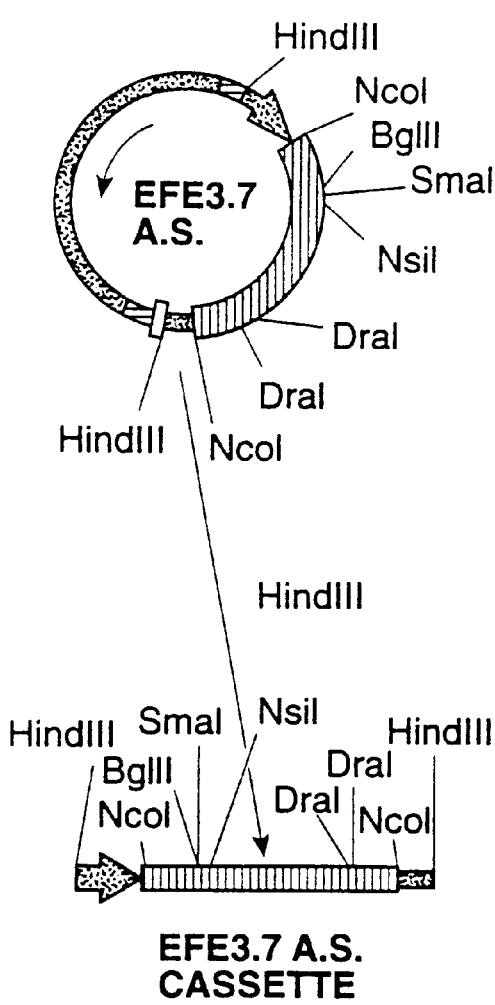
Figure 5C:
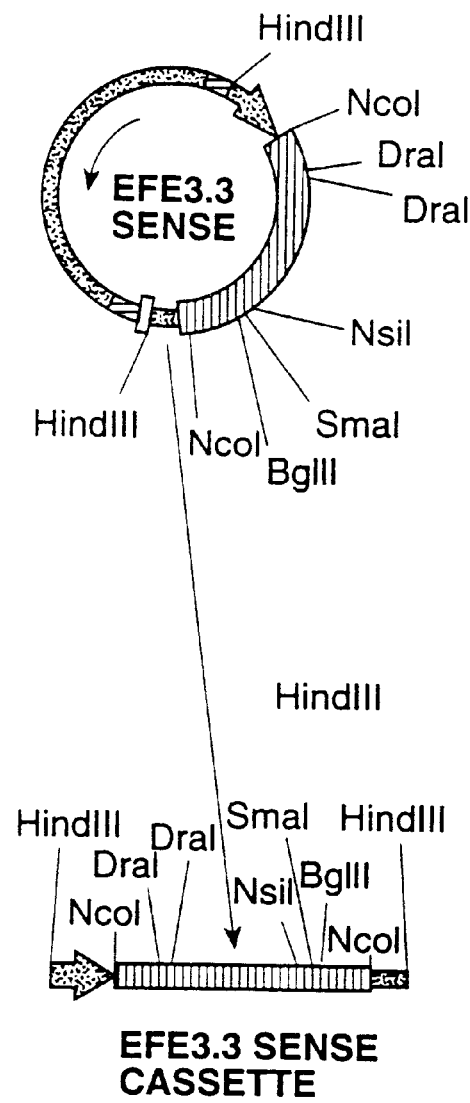
Figure 5D:
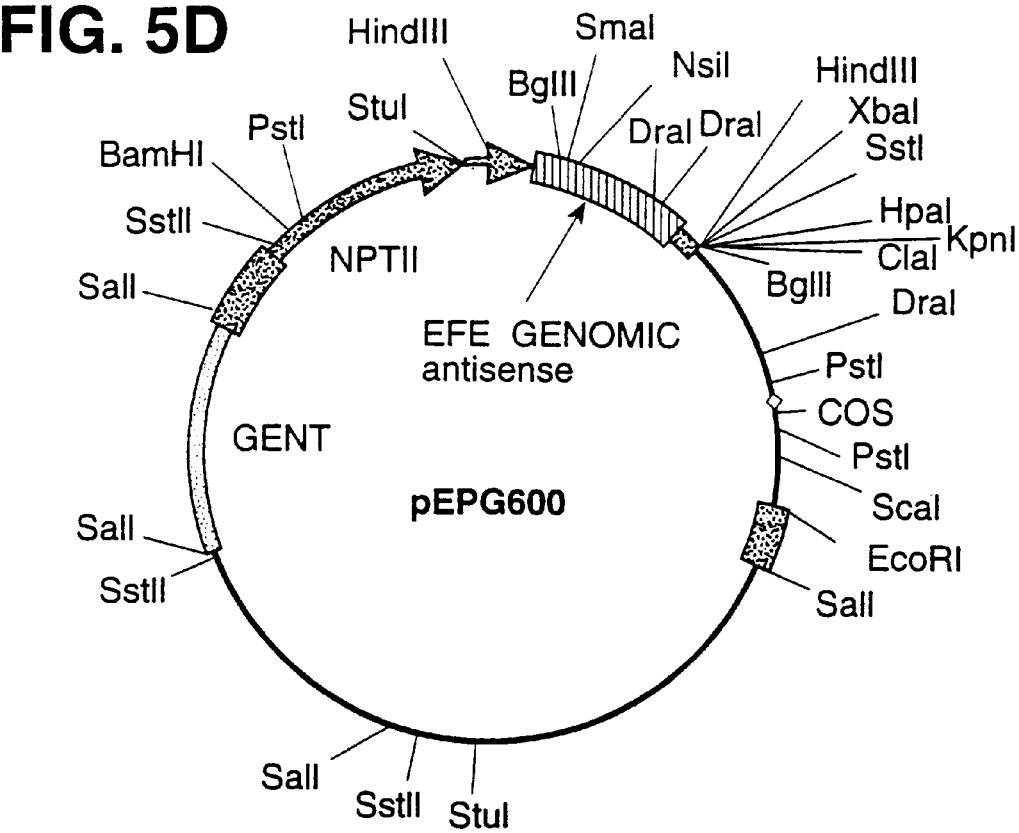
Figure 5E:
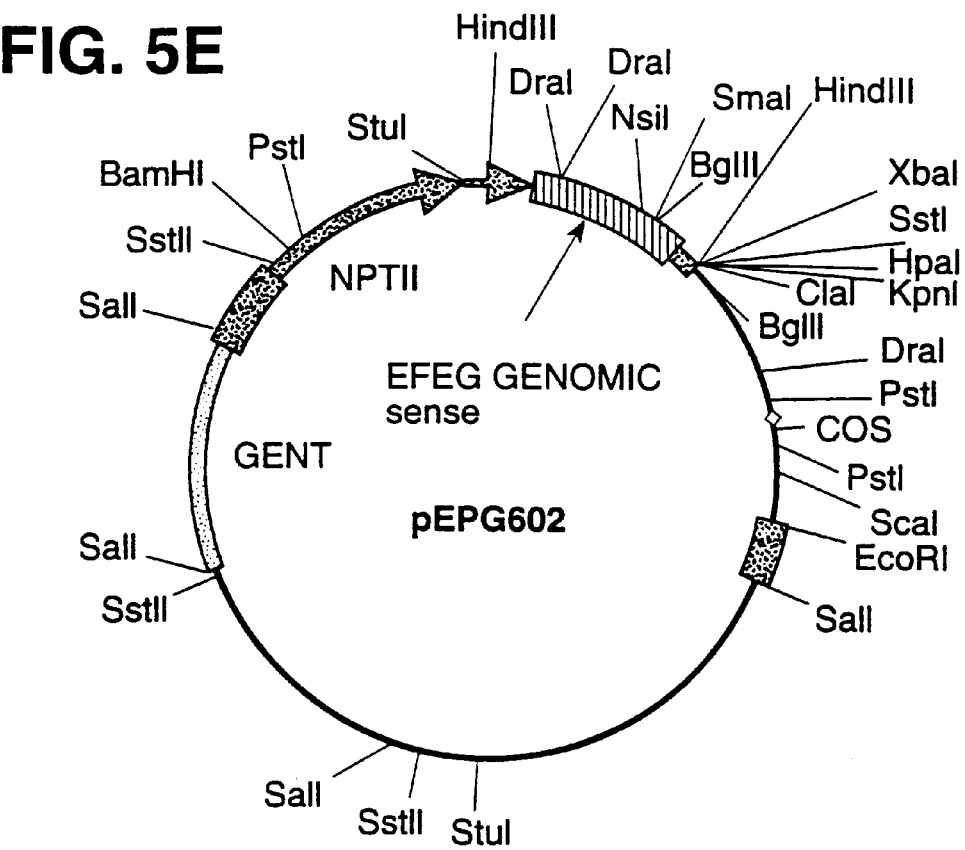

The 1 kb ACC oxidase PCR fragment was cloned into the pCRII™ vector, included in the TA Cloning Kit available from Invitrogen Corporation (San Diego, Calif.) to obtain a clone known as EFEG3 (FIG. 4). The sequence of the inserted gene in EFEG3 was verified by nucleotide DNA sequencing using a U.S. Biochemical (Cleveland, Ohio) dideoxy sequencing kit (FIG. 1) (SEQ ID NO:2).

EXAMPLE 6

Insertion of the ACC Oxidase Coding Sequence into an Expression Cassette (cp Express) in Antisense Orientation EcoRI digestion of clone EFEG3 produced an EFEG3 fragment containing the *Brassica aleracea* ACC oxidase gene. An NcoI restriction site was fitted onto the 3' end of the EFEG3 fragment during a second PCR amplification by the use of the primer RMM480 (5' CGGCATCTCTGAAA-GATTTTTGT<u>GGTACC</u>TCAAA 3', complementary to the 3' end of the ACC oxidase gene) (FIGS. 2 and 4) (SEQ ID NO:5). Its sequence is located at the 3' end of the gene and includes a novel NcoI site (FIGS. 2 and 4). During this second PCR amplification one of two internal NcoI sites was also eliminated by the use of oligomer primer RMM470 (5' GAGAG <u>CCATGG</u>AGAAGAACATTAAGTTTCCAGTTGTAGACT TGTCCAAGCTCATTGGTGAAGAGAGAGACCAAA <u>CAATGG</u>CTTTGATCAACGATGC 3', complementary to the 5' end of the ACC oxidase gene) (FIGS. 2 and 4) (SEQ ID NO:6); RMM470 does not include the first internal NcoI site located in EFEG3 (FIG. 2). The resulting PCR fragment was cloned into the pCRII cloning vector included in the TA cloning kit available from Invitrogen Corporation to obtain a clone known as EFEG3'.

To begin transfer of the *Brassica oleracea* cDNA ACC oxidase gene into a plant expression cassette, EFEG3' was digested with NcoI to produce an NcoI cDNA fragment encoding *B. oleracea* ACC oxidase. Using standard methods (see J. L.-Slightom, 1991, *Gene,* Vol. 100, pp. 251–255, "Custom PCR Engineering of a Plant Expression Vector"), this fragment was inserted into the expression cassette pUC18cp express in an antisense orientation to obtain EFEG3ce1 and in the sense orientation to obtain EFEG3ce7 (FIG. 4). pUC18cp express includes about 330 base pairs of the CaMV 35S transcript promoter and 70 bp of the cucumber mosaic virus 5'-untranslated region. The region flanking the 3' end of the inserted gene includes 200 bp of the CaMV35S transcript poly(A) addition signal. The Nco I site maintains the ATG translation initiation site found in the ACC oxidase gene. Sense orientation constructs are designed to give sense mRNA that can be translated into ACC oxidase in the plant. The antisense orientation of the NcoI fragment in EFEG3ce1 is designed to transcribe mRNA in the plant that is complementary to the sense mRNA; no *B. oleracea* ACC oxidase protein can be translated in the plant from this construct.

EXAMPLE 7

Insertion of ACC Oxidase DNA Cassettes into a Binary Vector

The antisense cassette EFEG3FL AS (FIG. 4) was inserted into the unique HindIII site of binary vector pGA482G to produce plasmid pEPG604 (FIG. 4). pGA482G is available from Gynehung An, Institute of Biological Chemistry, Washington State University in the form of pGA482 followed by the insertion of a gentamicin resistance gene. The sense cassette EFEG3FL (FIG. 4) was inserted into the unique HindIII site of binary vector pGA482G to produce plasmid pEPG606 (FIG. 4). The structures shown in FIG. 4 were verified by restriction analysis.

EXAMPLE 8

Transformation of the Binary Vectors into *Brassica oleracea* Plants by Agrobacteria-mediated Transformation The binary plasmids pEPG604 and pEPG606 are transformed into strains of *Agrobacterium tumefaciens,* e.g., strain C58Z707 and *Agrobacterium rhizogenes,* e.g., strain $A_4$. Strain C58Z707 is available from Augus Hebpurn at Indiana University, Bloomington, Ind. (Hepburn et al., (1985) *J. Gen. Micro.* 131:2961–2969). Strain $A_4$ is available from Jerry Slightom, The Upjohn Company, Kalamazoo, Mich. Evidence of the origin of the strain $A_4$ is presented by Slightom et al. *J. Biol. Chem.* (1986) Vol. 261, No. 1 pp. 108–121. The resulting Agrobacterium strain is used to perform *B. oleracea* plant transformation procedures.

Agrobacterium-mediated transfer of the plant expressible *Brassica oleracea* ACC oxidase is done using procedures known to those skilled in the art. For example, David and Tempe (1988) *Plant Cell Reports* 7:88–91) and Damgaard and Rasmussen (1991) *Plant Molecular Biology* 17:1–8, transformed cauliflower and rapeseed hypocotyl cells and regenerated transformed plants. Specifically, aseptically grown hypocotyls with or without an intact root system are inoculated with engineered *A. tumefaciens* or *A. rhizogene.* Hypocotyls are then transferred to Murashiges and Shogg (1962) *Physiol Plantarum* 15:473–497) medium (MS) containing 200 micromolar acetsyringone. Two to three days later, hypocotyls are transferred to MS medium containing 50 mg/1 kanamycin sulfate, 500 mg/1 carbenicillin and 200 mg/1 cefotaxime (MS-O). Hypocotyls are continuously subcultured every 21 days on MS-O medium until shoots form. Shoots are then removed from agar and potted in soil. Transgenic plants ($R_0$) are grown to sexual maturity in a green house and $R_1$ transgeneic seed is produced. Transfer of this gene into plant cells can also be accomplished using other methods, such as direct DNA uptake (Paszkowski, et al, *EMBO J.,* 1084, 3:2717), microinjection (Crossway, et al., *Mol Gen. Genet.* 202:179), electroporation (Fromm et al., *Proc. Natl. Acad. Sci. U.S.A.* 82:5824), or high velocity microprojectiles (Klein, et al., Nature 327:70).

EXAMPLE 9

Evaluation of Transgenic Plants for Inhibition of Ethylene Biosynthesis

Transgenic status of $R_0$ plants and their segregating progeny is verified by routine methods. These include ELISA assays for NPTII protein detection; DNA assays such as PCR amplification (detection) of transgenes and Southern blot hybridization for detection of transgenes.

For example, protein in leaf tissue samples taken from R1 transgenic lettuce seedlings is extracted and analyzed for NPTII protein by enzyme-linked immunosorbant assay (ELISA). The procedure and kit supplied by 5 Prime→3 Prime, Inc., Boulder, Colo., is used to assay NPTII expression in R1 transgenic lettuce seedlings. In an initial screen of R1 transgenic seedlings for NPTII protein by ELISA, it is expected that 11 independent transgenic proprietary B. olerace lines express NPTII. The date indicate that these initial lines are segregating for the NPTII marker gene.

Evaluation of transgenic plants for inhibition of ethylene biosynthesis can be accomplished by assaying transgenic B. oleacea materials for expression of ACC oxidase antisense RNA using a Northern analysis or a RNase protection assay. In a Northern analysis of transgenic materials, RNA extracted from transgenic B. oleracea is subjected to agarose electrophoresis and blotted onto a Nylon membrane. A radioactive ($^{32}$P-labelled) RNA probe (sense RNA) synthesized in vitro is used to hybridize the blot. Only antisense RNA of the ACC oxidase trangene in the plant will bind to the $^{32}$P-labelled RNA probe; thus antisense ACC oxidase RNA will be detected by autoradiography. Parallel hybridization of replicate blots with antisense ACC oxidase RNA probe serves as a check on the hybridization with the sense RNA probe.

The RNase protection assay involves hybridizing a labelled RNA molecule (pure sequence synthesized in vitro) with total tissue RNA in solution in a tube. Only complementary RNA will hybridize with the pure RNA labelled and sythesized in vitro. The total pool of RNA is subjected to RNase A and RNase $T_1$ digestion; protected mRNAs are resistant to RNase digestion. Protected mRNAa are evaluated quantitatively and qualitatively on an acrylamide gel.

Following the determination of whether B. oleracea ACC oxidase antisense RNA is expressed, the transgenic materials or tissues are assayed for ACC oxidase activity. This can be accomplished by the assay methods outlined above for measuring ACC oxidase activity. In addition, it is possible to employ immunological methods (for example, ELISA or Western blots) to assay transgenic materials for levels of ACC oxidase protein. It is expected that transgenic would exhibit reduced levels of ACC oxidase protein compared with non-transgenic materials. Tian et al. (1994) *J. Amer. Soc. Hort. Sci.* Vol. 119:276–281 outline in some detail their procedures for evaluating "degreening" in response to ethylene in harvested broccoli. They measured chlorophyll content in the florets after harvest.

ACC OXIDASE GENE OBTAINED FROM B. OLERACEA GENOMIC CLONES

EXAMPLE 10

Extraction of Total Cellular DNA from Broccoli by a CTAB Extraction Method

Three or 4 newly expanding leaves (0.5–1 gm fresh weight) were placed into the bottom corner of a Ziplock bag. One mL of preheated CTAB extraction buffer was added to the leaf sample. CTAB extraction buffer (1% (w/v) CTAB Sigma H-5882; 1.4 M NaCl; 100 mM Tris HCl pH 8.0; 30 mM EDTA pH 8.0) was prepared and preheated to 65° C. 5–10 minutes prior to use. The following was added to each mL of CTAB extraction buffer just before using: 10 uL of 2-mercaptoethanol, 6 µL of Ribonuclease $T_1$ (5,000 U/ml) Sigma R-8251, and 25 µL of Ribonuclease A(10 mg/ml) Sigma R-4875.

The Ziplock bag was placed flat on a hard surface. A one-liter Corning media-bottle was firmly rolled across the surface of the bag repeatedly until the leaf tissue was disrupted and had the consistency of applesauce. The macerated sample was moved to a bottom corner of the Ziplock bag and the corner was cut with a scissors. The entire sample was squeezed into a sterile 15-mL Falcon tube and incubated at 70° C. for 30 minutes. The sample was cooled for 5 minutes at room temperature. One mL of cholororm-octanol (24:1, V:V) was added, and the sample was vortexed 1 second to mix thoroughly. The samples were then centrifuged in a Beckman GH 3.7 rotor (Beckman GPR centrifuge) at 2500 rpm, 25° C. for 5 minutes to separate phases. The aqueous phase (~1000 µl) was then transferred to a sterile 1.5-mL Eppendorf tube. 1.5 µL of RNAse $T_1$ (10 mg/mL) was added. An equal volume of 1% CTAB precipitation buffer was added to each sample. The tube was inverted a few times and incubated at room temperature for 30 minutes.

The sample was centrifuged in a Eppendorf microfuge for 60 seconds to pellet the precipitate. The supernatant was discarded, and the tube was inverted on a paper towel to drain. 500 µl of high salt solution (10 mM Tris pH 8.0, 1 M NaCl, 1 mM EDTA pH 8.0) was added, and the sample was incubated at 65° C. for 15 minutes to dissolve the DNA. One ml of 100% ethanol was added and the sample was placed at −20° C. for one hour or overnight to precipitate DNA. DNA was hooked or spooled with a 1.5 ml capillary pipet and placed into a sterile 1.5 ml Eppendorf tube. The DNA pellet was washed by adding 1 ml of wash solution (80% ethanol, 15 mM ammonium acetate) and incubated at room temperature 15 minutes. The washed DNA was dissolved in 300 µL of sterile water.

EXAMPLE 11

PCR Amplification of Target Genomic ACC Oxidase

Polymerase chain reactions (PCRs) were carried out using reagents supplied with the Perkin Elmer Cetus Gene Amp PCR Kit under the following conditions: ~0.1 ug/mL total cellular DNA of *Brassica oleracea* 1.5 mM $MgCl_2$, 24 ug/mL of each oligomer primer, 200 uM each dNPT, kit reaction buffer, and AmpliTaq DNA polymerase supplied with the kit. Reaction tubes were subject to 93° C. for 1 min, 55° C. for 1 min., the 72° C. for 3 min. for 30 cycles in a Perkin Lemer Thermocycler. Oligonucleotides used to prime the PCR were modeled after sequences of a cDNA close of the ACC oxidase gene found in *Brassica juncea* (Pua et al. (1992) *Plant Mol. Biology* 19:541–544). Oligomer primers RMM389 (5' GAGAGAGCCATGGAGAAGAACAT-TAAGTTTCCAG 3', complementary to the 5' end of the cDNA clone of *Brassica juncea* ACC oxidase gene) (SEQ ID NO:3) AND rmm390 (5' CCGCCAATTAACAACCAG-GTACCACAAATTTCACACCC 3', complementary to the 3' end of the cDNA clone of *Brassica juncea* ACC oxidase gene) (SEQ ID NO:7) were used to prime this reaction. (FIG. 3).

EXAMPLE 12

Cloning Genomic ACC Oxidase PCR Fragment into the pCRII Vector

The genomic ACC oxidase PCR fragment was cloned into the pCRII vector (Invitrogen Corporation, San Diego, Calif.) to obtain a clone known as EFE3-1 (FIG. 5). The sequence of the insert gene in EFE3-1 was verified by nucleotide DNA sequencing using a U.F. Biochemical (Cleveland, Ohio) dideoxy sequencing kit (FIG. 3) (SEQ ID NO:8). Comparison of *B. oleracea* genomic clone EFE3-1 [SEQ ID NO:11] with cDNA clone EFEG-3 [SEQ ID NO:12] revealed 4 exons and 3 introns in *B. oleracea* ACC oxidase genomic clone 3-1 (FIG. 3). The coding regions of genomic clone 3-1 are identical to the sequence for the cDNA clone EFEG-3 (FIG. 3). The structure of *Brassica oleracea* ACC oxidase is highly related to the intron/exon arrangement in the tomato genomic ACC oxidase clone GTOMA (Holdsworth et al. (1987) *Nuc. Acids Res.* 15:10600).

EXAMPLE 13

Insertion of the ACC Oxidase Coding Sequence into an Expression Cassette (cp Express)

To begin transfer of the genomic *Brassica oleracea* ACC oxidase gene into a plant expression cassette, EFE3-1 was digested with NcoI to produce a 1528 bp NcoI fragment encoding genomic *B. oleracea* ACC oxidase; two internal NcoI sites near the 5' end of the gene resulted in the elimination of about 220 bp of the gene by NcoI digestion (FIGS. 3 and 5). Using standard methods (see J. L. Slightom, 1991, *Gene.* Vol. 100, pp. 251–255), this fragment was inserted into the expression cassette pUC18cp express in an antisense orientation to obtain EFE2.7 and in the sense orientation to obtain EFE3.3 (FIG. 5).

EXAMPLE 14

Insertion of Genomic ACC Oxidase DNA Cassettes into a Binary Vector

HindIII fragments harboring full-length cDNA clone antisense and sense cassettes were isolated. The antisense cassette EFE3.7 AS (FIG. 5) was inserted into the unique HindIII site of binary vector pGA482G to produce plasmid pEPG600 (FIG. 5). The sense cassette EFE3.3 SENSE (FIG. 5) was inserted into the unique HindIII site of binary vector pGA482G to produce plasmid pEPG602 (FIG. 5). The structures shown in FIG. 5 were verified by restriction analysis.

EXAMPLE 15

Transformation of the Binary Vectors into *Brassica oleracea* Plants by Agrobacteria-mediated Transformation Procedures The binary plasmids are transformed into Agrobacterium strains $A_4$ and C58Z707 as in Example 8. The resulting Agrobacterium strain is used to perform *B. oleracea* plant transformation procedures.

EXAMPLE 16

Evaluation of Transgenic Plants for Inhibition of Ethylene Biosynthesis

Evaluation of transgenic plants for inhibition of ethylene biosynthesis is accomplished as described in Example 9.

EXAMPLE 17

*Brassica oleracea* ACC oxidase antisense constructs were transferred to melon (*Cucumis melo*) plants via Agrobacteria-mediated transformation using procedures published by Fang and Grumet (1990 and 1993). The pEPG600 and pEPG604 constructs were transformed into melon (see FIGS. 4 and 5 for restriction maps of thesa binary plasmids).

After shoots were regenerated on kanamycin-containing solid tissue culture media, they were rooted and tested for transformation status. We verified transformation status either by testing regenerated organized shoots for ability to form callus on kanamycin-containing solid media (only transformed materials expressing NPTII can grow on these media) or by NPTIII expression detected by ELISA. The results are summarized in Table I.

TABLE I

SUMMARY OF CANTALOUPE LINES TRANSFORMED WITH *B. OLERACEA* ACC OXIDASE CONSTRUCT

| Inbred | Exp. line | Construct | Ploidy | Plant Status | R1 Seed |
| --- | --- | --- | --- | --- | --- |
| 10 | 4140.3 | 604 | AB | discarded | |
| 10 | 4168.10 | 604 | | harvested | 0162 |
| 10 | 4168.11B | 604 | | potted | |
| 10 | 4168.14 | 604 | | died | |
| 10 | 4168.15 | 604 | | died | |
| 10 | 4168.15B | 604 | | harvested | 0010 |
| 10 | 4168.17D | 604 | | potted | |
| 10 | 4168.18 | 604 | | harvested | 0016 |
| 10 | 4168.19 | 604 | | harvested | 0084 |
| 10 | 4168.20 | 604 | | harvested | 0146 |
| 10 | 4168.21B | 604 | AB | discarded | |
| 10 | 4168.22B | 604 | | harvested | 0173 |
| 10 | 4168.25B | 604 | | harvested | 0047 |
| 10 | 4168.29 | 604 | | died | |
| 10 | 4165.33 | 604 | | potted | |
| 10 | 4168.33B | 604 | | potted | |
| CA95 | 4132.6 | 600 | | potted | |
| CA95 | 4132.9 | 600 | | harvested | 0190 |

Accordingly, stable transgenic lines have been produced containing the ACC antisense constructs. Further, seed has been harvested from these plants.

EXAMPLE 18

ACC oxidase antisense transgene expression was evaluated in a number of $R_0$ and $R_1$ melon plants by Northern blot hybridization. This assay measures levels of accumulated *B. oleracea* ACC oxidase antisense RNA. RNA was extracted from transgenic *Cucumis melo* leaves with the use of an RNA extraction kit (Trireagent) supplied by Molecular Research Center, Inc. (Cincinnati, Ohio). Total melon leaf RNA was subjected to glyoxalation before separation by agarose gel electrophoresis. After electrophoresis, RNA was pressure blotted onto a Nylon membrane (Hybond N, Amersham) with the use a Stratagene pressure blotter (La Jolla, Calif.).

Radioactive ($^{32}$P-labelled) RNA probe (sense RNA) was synthesized in vitro with the use of RNA transcription vectors, for example pGEM-3 (Promega, Madison, Wis.). First the coding sequence for *B. oleracea* oxidase was inserted into the RNA transcription vector pGMM, a modification of pBluescript II SK (+). The pGMM plasmid harboring the ACC oxidase coding sequence was linearized with BamHI and used as template for sense RNA synthesis in vitro. Radioactive $^{32}$P-labelled probe was synthesized under the following reaction conditions: 2 µg linearized template DNA, T3/T7 buffer (1×) (BRL), 10 µL $\alpha^{32}$P-UTP, 10 mM dithiothreitol, 2 ul RNAsin (Promega, Madison, Wis.), 2 mM ATP, CTP, and GPT and 1 mM UTP, and 1 µl T7 RNA polymerase (BRL) in a 50-µl total reaction volume. Blots were hybridized at 65° C. with the use of Megablock (Cel Associates, Houston, Tex.) and instructions provided with the Megablock reagent. Following hybridization blots were washed according to instructions provided with Megablock reagent. Hybridization signals were detected by autoradiography. The results are summarized in Table II and Table III.

TABLE II

SUMMARY OF $R_0$ PLANT RNA BLOT RESULTS

| Species | Binary | Gene Construct | $R_0$Plant | Transcript? |
|---|---|---|---|---|
| Melon CA10 | pEPG 604 | EFE cCNA f1 AS | 4168-33 | (as−) |
| | | | 4168-11B | (as+) |
| | | | 4168-18 | (as+) |
| | | | 4168-19 | (as−) |
| | | | 4168-25B | (as−) |
| | | | 4168-35 | (as−) |
| | | | 4168-19 | (as−) |
| | | | 4168-10 | (as+) |
| | | | 4168-20 | (as+) |
| | | | 4168-15B | (as+) |

TABLE III

SUMMARY OF R1 PLANT RNA BLOT ANALYSIS

| Species | Binary | Gene Construct | $R_0$Plant | Transcript? | NPTII |
|---|---|---|---|---|---|
| Melon CA10 | pEPG 604 | EFE cCNA f1 AS | 4168-10-1 | (as−) | − |
| | | | 4168-10-2 | (as−) | + |
| | | | 4168-10-3 | (as−) | − |
| | | | 4168-10-4 | (as−) | − |
| | | | 4168-10-5 | (as+) | + |
| | | | 4168-10-6 | | + |
| | | | 4168-10-7 | (as+) | + |
| | | | 4168-10-8 | (as+) | + |
| | | | 4168-10-9 | | + |
| | | | 4168-10-11 | (as+) | |
| | | | 4168-19-12 | | + |
| | | | 4168-20-1 | (as+) | + |
| | | | 4168-20-2 | (as+) | + |
| | | | 4168-19-13 | | + |
| | | | 4168-19-14 | | + |
| | | | 4168-20-3 | | + |
| | | | 4168-20-4 | | + |
| | | | 4168-20-5 | (as+) | + |
| | | | 4168-20-6 | (as+) | + |
| | | | 4168-20-7 | (as+) | + |
| | | | 4168-20-8 | (as+) | + |
| | | | 4168-20-9 | (as+) | + |
| | | | 4168-20-10 | (as+) | + |
| | | | 4168-20-11 | (as+) | + |
| | | | 4168-20-12 | (as+) | + |
| | | | 4168-20-13 | (as+) | + |
| | | | 4168-20-14 | (as+) | + |
| | | | 4168-20-15 | (as+) | + |

Figure 6:
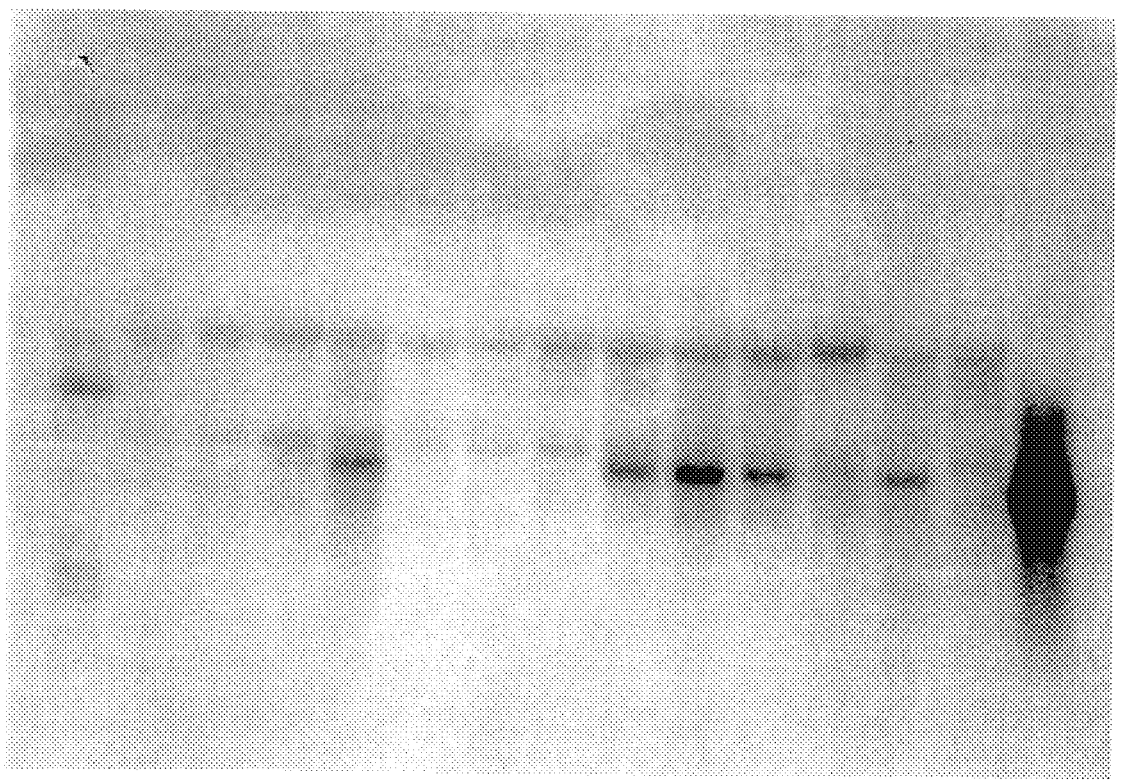
FIG. 6 illustrates an RNA blot of total RNA extracted from $R_0$ transgenic melon plants (leaves) hybridized with *B. oleracea* ACC oxidase sense RNA probe.
Figure 7:
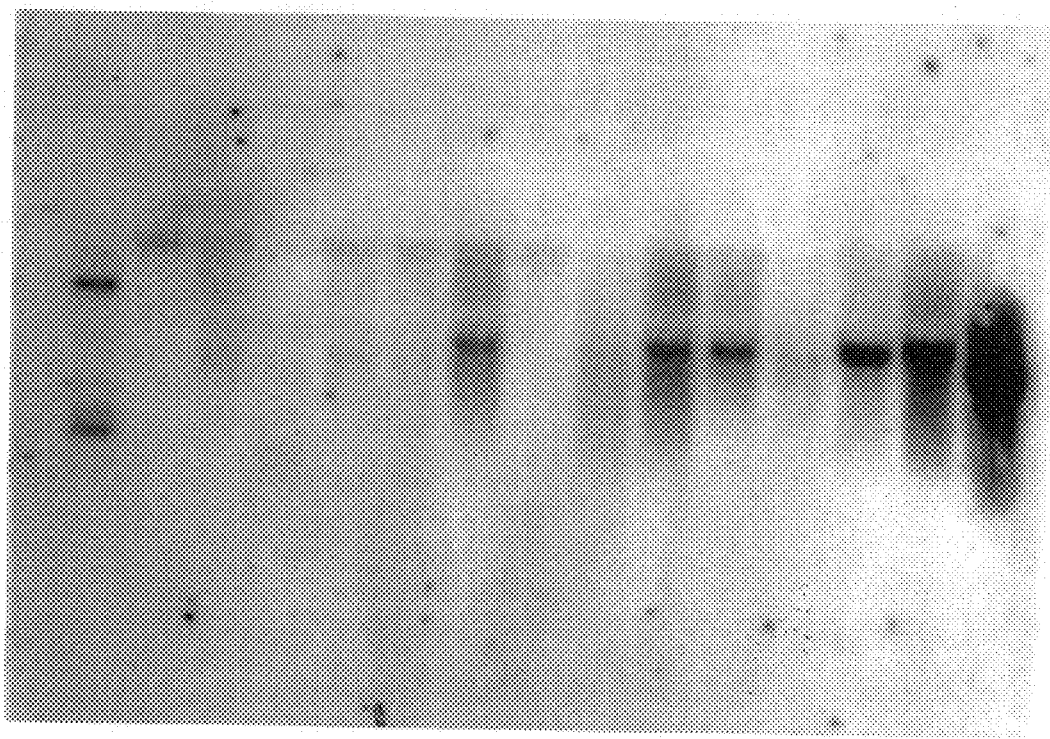
FIG. 7 illustrates an RNA blot of total RNA extracted from $R_1$ transgenic melon progeny of line 4168-10 hybridized with *B. oleracea* ACC oxidase sense RNA probe.
Figure 8:
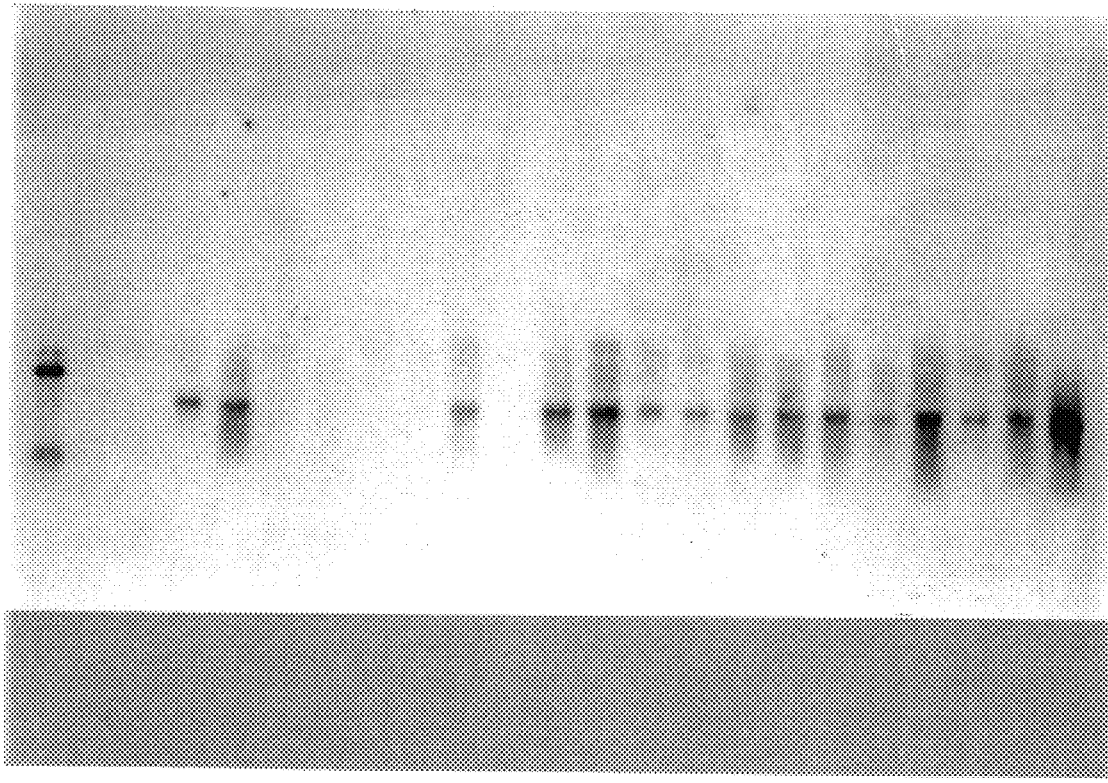
FIG. 8 illustrates an RNA blot of total RNA extracted form $R_1$ transgenic melon progeny of lines 4168-19 and 4168-20 hybridized with *B. oleracea* ACC oxidase sense RNA probe.

RNA blot analysis of melon plants transgenic for the *B. oleracea* ACC oxidase antisense construct in pEPG604 shows accumulation of ACC oxidase antisense RNA (FIGS. 6, 7, and 8). For example, transgenic $R_0$ melon plants 4168-18, 4168-10, 4168-20, and 4168-21 accumulate substantial levels of ACC oxidase antisense transcript (FIG. 6 and Table II).

FIG. 7 shows an autoradiogram of RNA blot of total RNA extracted from $R_0$ transgenic melon plants (leaves) hybridized with *B. oleracea* ACC oxidase sense RNA probe (approximately 50×10⁶ cpm $^{32}$P-labelled RNA probe). RNA extracted from melon plants transformed with virus coat protein cassettes and RNA extracted from red cabbage plants transformed with pEPG604 are also included Approximately 10 ug total plant RNA was loaded in each well. Lane 1, RNA MW Markers; lane 2, melon line CA10 transformed with pEPG328 (virus coated protein cassettes); lane 3, melon line CA40 transformed with pEPG328; lane 4, line 4168-11B; lane 5, line 4168-18; lane 6, 4168-19; lane 7, melon line 626 transformed with pEPG212 (virus coat protein cassettes); lane 8, CA10 melon nontransgenic control; lane 9, 4168-10; lane 10, 4168-20; lane 11, 4168-21; lane 12, 4168-15B; lane 13, red cabbage transgenic line 604-30 transformed with PEPG604; lane 14, nontransgenic red cabbage; lane 15, *B. oleracea* ACC oxidase antisense RNA synthesized in vitro; and lane 16, *B. oleacea* ACC oxidase sense RNA synthesized in vitro. Number 4168 refers to melon line CA10 transformed with PEPG604 (see Table II for details).

This result strongly indicates that *B. oleracea* ACC oxidase antisense constructs are actively transcribed after being transferred into melon.

RNA blot analysis of $R_1$ progeny of 4168-10, 4168-19, and 4168-20 shows that some progeny accumulate ACC oxidase antisense RNA to high levels, and others accumulate lower levels of antisense RNA (FIGS. 7 and 8 and Table III).

FIG. 7 shows an RNA blot of total RNA extracted from $R_1$ transgenic melon progeny of line 4168-10 hybridized with *B. oleracea* ACC oxidase sense RNA probe (about 50×10⁶ cpm $^{32}$P-labelled RNA probe). Approximately 10 ug total RNA was electrophoresed in each lane. Seed taken from a fruit produced on $R_0$ plant 4168-10 was germinated and RNA samples were extracted from seedlings for analysis. Lane 1, RNA MW markers; land 2, melon line CA10 transformed with pEPG328; lane 3, 4168-10-1; lane 4, 4168-10-2; lane 5, 4168-10-3; lane 6, 4168-10-4; lane 64168-10-4; lane 7, 4168-10-5; lane 8, CA10 transformed with pEPG196; lane 9, 4168-10-6; lane 10, 4168-10-7; lane 11, 4168-10-8; lane 12, 4168-10-9; lane 13, 4168-10-11; lane 14, 4168-18 $R_0$; lane 15, *B. oleracea* ACC oxidase antisense RNA synthesized in vitro; and lane 16, *B. oleracea* ACC oxidase sense RNA synthesized in vitro. Number 4168 refers to melon line CA10 transformed with PEPG604 (see Table II for details).

FIG. 8 shows an RNA blot of total RNA extracted from $R_1$ transgenic melon progeny of lines 4168-19 and 4168-20 hybridized with *B. oleracea* ACC oxidase sense RNA probe. Electrophoresis and hybridization conditions were similar to conditions used in FIGS. 3 and 4. Seed taken from produced on $R_0$ plants 4168-19 and 4168-20 was germinated and RNA samples were extracted from seedlings for analysis. Lane 1, RNA MW markers; Lane 2, CA10 transformed with PEPG328; lane 3, 4168--19-12; lane 4, 4168-20-1; lane 5, 4168-20-2lane 6, 4168-19-13; lane 7, 4168-19-14; lane 8, 4168-20-3; lane 9, 4168-20 -4; lane 10, 4168-20-5; lane 11, CA10 transformed with pEPG208; lane 12, 4168-20-6; lane 13, 4168-20-7; lane 14, 4168-20-8; lane 15, 4168-20-9; lane 16, 4168-20-10; lane 17, 4168-20-11; lane 18, 4168-20-12; lane 19, 4168-20-13; lane 20, 4168-20-14; lane 21, 4168-20-15; lane 22, 4168-18 $R_0$; lane 23, *B. oleracea* ACC oxidase antisense RNA synthesized in vitro; and lane 24, *B.*

*oleracea* ACC oxidase sense RNA synthesized in vitro. Numbers 4168-19 and 4168-20 refer to melon line CA10 transformed with PEPG604 (see Table II for details).

These results demonstrate clearly that the transgene is heritable and that it produces antisense RNA in $R_1$ progeny.

It is highly unlikely that the hybridization signals shown in FIGS. 6, 7, and 8 result from non-specific hybridization. Each RNA blot included an antisense and sense in vitro transcript of ACC oxidase (for example, lanes 15 and 16, respectively, in FIGS. 6 and 7). ACC oxidase sense RNA in vitro transcript probe hybridized specifically with antisense in vitro transcript (for example, see FIGS. 6 and 7, lanes 15 and 16). The sense RNA transcript probe did not hybridize with blotted antisense transcript (FIGS. 6, and 7, lane 16).

Hybridizations signals produced in RNA extracted from nontransgenic red cabbage, melons, and broccoli were compared with RNA extracted from pEPG604-transformed red cabbage melons, and broccoli. Only RNA samples extracted from transgenic plants produced an ACC oxidase antisense signal (for example, FIG. 6, lanes 13 and 14).

The mobility of ACC oxidase antisense transcripts produced from the cassette in pEPG604 (ACC oxidase full length antisense) were also compared with transcripts produced from the cassette in pEPG608 (ACC oxidase truncated antisense) following transformation into red cabbage. ACC oxidase transcripts detected in red cabbage plants transformed with the full length construct are longer than the transcripts detected in red cabbage plants transformed with the truncated ACC oxidase construct. This result demonstrates conclusively that the sense RNA problem is detecting only ACC oxidase antisense RNA transcripts.

These results demonstrate that only antisense RNA transcribed by the *B. oleracea* ACC oxidase transgene in the plant is being detected by the $^{32}$P-labelled RNA probe.

Lack of detectable ACC oxidase antisense accumulation does not indicate that the transgene will be ineffective in inhibiting ethylene biosynthetic pathway gene expression. Published results indicate that the degree of endogenous sense RNA reduction is not related to levels of antisense RNA accumulation (for example, see Stockhaus et al., 1990). Endogenous melon ACC oxidase mRNA is produced in transgenic lines.

Melon, red cabbage, and broccoli plants transformed with pEPG610 and pEPG612 are analyzed in the same way. These binary plasmids include ACC synthase antisense RNA constructs. The analysis includes Northern analysis to evaluate *B. oleracea* ACC synthase antisense RNA accumulation and reduction in levels of endogenous ACC synthase antisense RNA accumulation and reduction in levels of endogenous ACC synthase sense RNA levels. The analysis shows expression of RNA in these plants.

While specific embodiments of the invention have been described, it should be apparent to those skilled in the art that various modifications thereof can be made without departing from the true spirit and scope of the invention. Accordingly, it is intended that the following claims cover all such modifications with the full inventive concept.

A. One of our first goals was to determine whether our ACC oxidase constructs produce antisense RNA in a transgenic situation. To answer this question, we transformed ACC oxidase constructs into red cabbage. Transgenic red cabbage lines were generated with the use of the following binary plasmids; pEPG600, 604, 606, and 608. We verified the transgenic status of many of the plants by NPTII ELISA and PCR analysis of the ACC oxidase transgene. These are summarized in the Tables.

B. Next we isolated, electrophoresed, and blotted total RNA by methods described in the melon ACC oxidase disclosure. Antisense ACC oxidase RNA transcripts were detected in RNA extracted from plants transformed with pEPG604 and 608 (see Tables).

C. We next verified unambiguously that hybridization signals detected in total RNA of red cabbage $R_0$ transgenics correspond to *Brassica oleracea* ACC oxidase antisense messenger RNA. We analyzed cabbage $R_0$ plants transformed with pEPG604 (ACC oxidase full-length CDNA AS cassette) and plants transformed with pEPG608 (ACC oxidase truncated cDNA AS cassette). We electrophoresed both "604" and "608" transgenic RNAs on the same gel to compare mobilities of transgene messages produced by the full length and the truncated genes. The resulting blot clearly shows smaller messages in the "608" transgenic RNA's and longer messages in the "604" RNA's. This hybridization result can only be explained by expression of ACC oxidase antisense genes.

D. Brocoli plants transgenic for ACC oxidase constructs have also been obtained. These include the following lines:

| Transgenic Line Number | pEPG Construct | Status |
|---|---|---|
| 173-10 | 604 | potted |
| 133-1 | 604 | potted |
| 173-50 | 604 | potted |
| 173-40 | 604 | potted |
| 173-20 | 604 | potted |
| 133-19 | 604 | potted |
| 224-55 | 604 | potted |
| 238-33 | 604 | potted |
| 294-77 | 600 | potted |
| 287-68 | 600 | potted |
| 294-99 | 600 | potted |
| 238-6 | 604 | potted |
| 266-7 | 604 | potted |
| 133-22 | 604 | potted |
| 294-45 | 600 | potted |
| 224-81 | 604 | potted |
| 290-9 | 600 | potted |
| 224-62 | 604 | potted |
| 133-14 | 604 | potted |
| 294-27 | 600 | potted |
| 287-67 | 600 | potted |
| 294-53 | 600 | potted |
| 294-84 | 600 | potted |
| 294-88 | 600 | potted |
| 238-77 | 604 | potted |
| 287-72 | 600 | shoots |
| 238-77 | 604 | shoots |
| 294-144 | 600 | shoots |
| 294-35 | 600 | shoots |
| 294-3 | 600 | shoots |
| 287-36 | 600 | shoots |
| 287-123 | 600 | shoots |
| 294-122 | 600 | shoots |
| 294-109 | 600 | shoots |
| 294-4 | 600 | shoots |
| 294-47 | 600 | shoots |

| TRANSGENIC RED-CABBAGE EVALUATION | | | | |
|---|---|---|---|---|
| Germ-line: (16)NC9317424 | | | Gene construct: pEPG606 | |
| | NPTII | | PCR-Gene | |
| Transformant # | ELISA | PCR | presence | RNA Transcript |
| 606-1 | 0.329 | | | blot 11:?? |
| 606-2 | 1.298 | | | blot 12: degraded RNA |
| 606-3 | 1.028 | | | blot 12:?? |

TRANSGENIC RED-CABBAGE EVALUATION

Germ-line: (15)NC9317405    Gene construct: pEPG608

| Transformant # | NPTII ELISA | PCR | PCR-Gene presence | RNA Transcript |
|---|---|---|---|---|
| 608-1 | 1.398 | | | blots 7 & 12: AS+ |
| 608-2 | 0.334 | | | no RNA |
| 608-3 | 1.776 | | | blot 7: AS+ |
| 608-4 | 1.649 | | | blot 7: AS+ |
| 608-5 | 1.651 | | | blot 6 |
| 608-6 | 1.681 | | | not tested |
| 608-7 | 1.924 | | | blot 13: AS+ |
| 608-8 | 1.743 | | | no RNA |
| 608-9 | 1.909 | | | no RNA |
| 608-10 | 1.210 | | | no RNA |
| 608-11 | 1.555 | | | blot 12: AS+ |
| 608-12 | 0.007 | | | blot 13: AS+ |
| 608-13 | 0.828 | | | blot 13: AS+ |
| 608-14 | 1.892 | | | no RNA |
| 608-15 | 1.725 | | | not tested |
| 608-16 | | | | blot 12:AS+ |
| 608-17 | | | | blot 13:AS+ |

Germ-line: (4)PC929090    Gene construct: pEPG600

| Transformant # | NPTII ELISA | PCR | PCR-Gene presence | RNA Transcript |
|---|---|---|---|---|
| 600-1 | 1.545 | | | blot 12: AS− |
| 600-2 | 1.472 | | | blot 12: AS− |
| 600-3 | 1.792 | | | no RNA |
| 600-4 | 1.801 | | | no RNA |
| 600-5 | not tested | | | not tested |
| 600-6 | not tested | | | not tested |

Germ-line: (16)NC931724    Gene construct: pEPG604

| Transformant # | NPTII ELISA | PCR | PCR-Gene presence | RNA Transcript |
|---|---|---|---|---|
| 604-1 | 1.300 | − | − | blot 8: AS+ |
| 604-2 | 0.557 | + | + | blot 9: AS? |
| 604-3 | 0.573 | + | + | blot 9: AS+ |
| 604-4 | 0.757 | + | + | |
| 604-5 | 0.973 | + | + | blot 8: AS+ |
| 604-6 | 0.670 | + | + | blot 8: AS? |
| 604-7 | 1.041 | + | + | blots 8 & 13: AS? |
| 604-8 | 1.632 | + | + | blot 9: AS? |
| 604-9 | 1.406 | + | + | blot 9: AS+ |
| 604-10 | 1.007 | + | + | blot 8: AS+ |
| 604-11 | 1.131 | + | + | blot 9: AS+ |
| 604-12 | 0.552 | − | − | blot 9: degraded RNA |
| 604-13A,B | 1.125 | ++ | ++ | blot 9: AS+ |
| 604-14 | 1.004 | + | + | blot 11: degraded |
| 604-15 | 1.153 | − | − | blots 6 & 7: AS+ |
| 604-16 | 1.291 | + | + | blot 11: degraded RNA |
| 604-17 | 0.043 | + | − | |
| 604-18 | 0.277 | + | + | blot 8: AS+ |
| 604-19 | 1.329 | − | − | blot 8: AS+ |
| 604-20 | 0.911 | + | + | blot 10: AS+ |
| 604-21 | 1.479 | + | + | blot 10: AS+ |
| 604-22 | 1.535 | + | + | blot 10: AS− |
| 604-23 | 1.486 | + | + | blot 13: degraded RNA |
| 604-24 | 1.037 | + | + | blot 10: AS− |
| 604-1 | 1.300 | − | − | blot 8: AS + |
| 604-25 | 1.556 | + | + | blot 13: AS? |
| 604-26 | 1.704 | + | + | blots 10 & 11: AS+ |
| 604-27 | 1.537 | + | + | blot 12: AS+ |
| 604-28 | 1.293 | + | + | blots 6 & 7: AS+ |
| 604-29 | 1.702 | − | − | blots 6 & 11: AS + |
| 604-30 | 1.178 | + | + | blots 6 & 7: AS+ |
| 604-31 | 1.810 | + | + | blot 10: AS+ |
| 604-32 | 1.575 | + | + | not tested |
| 604-33 | 1.597 | + | + | blot 10: AS− |
| 604-34 | | + | + | blot 11: degraded RNA |
| 604-35 | | − | − | blots 6, 7, 11, 15: AS + |
| 604-36 | | + | + | blot 10: AS+ |
| 604-37 | | − | + | blot 10: AS− |
| 604-38 | | + | + | not test |
| 604-39 | | + | + | no RNA |
| 604-40 | not tested | | | not tested |
| 604-41 | not tested | | | not tested |
| 604-42 | | | | |
| 604-43 | | | | |
| 604-44 | | | | |

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 320 amino acids
      (B) TYPE: amino acid
      (C) STRANDEDNESS:
      (D) TOPOLOGY: linear (ii) MOLECULE TYPE: protein (xi) SEQUENCE DESCRIPTION: SEQ ID NO:1:

```
Met Glu Lys Asn Ile Lys Phe Pro Val Val Asp Leu Ser Lys Leu Ile
1               5                   10                  15

Gly Glu Glu Arg Asp Gln Thr Met Ala Leu Ile Asn Asp Ala Cys Glu
            20                  25                  30

Asn Trp Gly Phe Phe Glu Ile Val Asn His Gly Leu Pro His Asp Leu
            35                  40                  45

Met Asp Asn Val Glu Lys Met Thr Lys Glu His Tyr Lys Ile Ser Met
50                  55                  60

Glu Gln Lys Phe Asn Asp Met Leu Lys Ser Lys Gly Leu Glu Asn Leu
65                  70                  75                  80

Glu Arg Glu Val Glu Asp Val Asp Trp Glu Ser Thr Phe Tyr Leu Arg
                85                  90                  95

His Leu Pro Gln Ser Asn Leu Tyr Asp Ile Pro Asp Met Ser Asp Glu
            100                 105                 110

Tyr Arg Thr Ala Met Lys Asp Phe Gly Lys Arg Leu Glu Asn Leu Ala
            115                 120                 125

Glu Asp Leu Leu Asp Leu Leu Cys Glu Asn Leu Gly Leu Glu Lys Gly
130                 135                 140

Tyr Leu Lys Lys Val Phe His Gly Thr Lys Gly Pro Thr Phe Gly Thr
145                 150                 155                 160

Lys Val Ser Asn Tyr Pro Ala Cys Pro Lys Pro Glu Met Ile Lys Gly
                165                 170                 175

Leu Arg Ala His Thr Asp Ala Gly Gly Ile Ile Leu Leu Phe Gln Asp
            180                 185                 190

Asp Lys Val Ser Gly Leu Gln Leu Leu Lys Asp Gly Asp Trp Ile Asp
            195                 200                 205

Val Pro Pro Leu Asn His Ser Ile Val Ile Asn Leu Gly Asp Gln Leu
210                 215                 220

Glu Val Ile Thr Asn Gly Arg Tyr Lys Ser Val Met His Arg Val Val
225                 230                 235                 240

Thr Gln Lys Glu Gly Asn Arg Met Ser Ile Ala Ser Phe Tyr Asn Pro
                245                 250                 255

Gly Ser Asp Ala Glu Ile Ser Pro Ala Ser Ser Leu Ala Cys Lys Glu
            260                 265                 270

Thr Glu Tyr Pro Ser Phe Val Phe Asp Asp Tyr Met Lys Leu Tyr Ala
            275                 280                 285

Gly Val Lys Phe Gln Pro Lys Gly Pro Arg Phe Glu Ala Met Lys Asn
            290                 295                 300

Ala Asn Ala Val Thr Glu Leu Asn Pro Thr Ala Ala Val Glu Thr Phe
305                 310                 315                 320

(2) INFORMATION FOR SEQ ID NO:2:

(i) SEQUENCE CHARACTERISTICS:
        (A) LENGTH: 976 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Brassica oleracea
```

(ix) FEATURE:
    (A) NAME/KEY: CDS
    (B) LOCATION: 3..962

(xi) SEQUENCE DESCRIPTION: SEQ ID NO:2:

```
CC ATG GAG AAG AAC ATT AAG TTT CCA GTT GTA GAC TTG TCC AAG CTC        47
   Met Glu Lys Asn Ile Lys Phe Pro Val Val Asp Leu Ser Lys Leu
   1               5                   10                  15

ATT GGT GAA GAG AGA GAC CAA ACC ATG GCT TTG ATC AAC GAT GCT TGT       95
Ile Gly Glu Glu Arg Asp Gln Thr Met Ala Leu Ile Asn Asp Ala Cys
                20                  25                  30

GAG AAT TGG GGC TTC TTT GAG ATA GTG AAC CAT GGT TTA CCA CAT GAT      143
Glu Asn Trp Gly Phe Phe Glu Ile Val Asn His Gly Leu Pro His Asp
            35                  40                  45

TTG ATG GAC AAC GTC GAG AAG ATG ACA AAG GAA CAT TAC AAG ATA TCA      191
Leu Met Asp Asn Val Glu Lys Met Thr Lys Glu His Tyr Lys Ile Ser
        50                  55                  60

ATG GAA CAA AAG TTC AAC GAC ATG CTC AAA TCA AAA GGT TTG GAA AAT      239
Met Glu Gln Lys Phe Asn Asp Met Leu Lys Ser Lys Gly Leu Glu Asn
65                  70                  75

CTT GAG AGA GAA GTT GAG GAT GTT GAT TGG GAA AGC ACT TTC TAC CTT      287
Leu Glu Arg Glu Val Glu Asp Val Asp Trp Glu Ser Thr Phe Tyr Leu
80                  85                  90                  95

CGT CAT CTC CCT CAG TCC AAT CTC TAC GAC ATT CCT GAT ATG TCT GAT      335
Arg His Leu Pro Gln Ser Asn Leu Tyr Asp Ile Pro Asp Met Ser Asp
                100                 105                 110

GAA TAC CGG ACG GCC ATG AAA GAT TTT GGG AAG AGA TTG GAG AAT CTT      383
Glu Tyr Arg Thr Ala Met Lys Asp Phe Gly Lys Arg Leu Glu Asn Leu
            115                 120                 125

GCT GAG GAT TTG TTG GAT CTA TTG TGT GAG AAT TTA GGG TTA GAG AAA      431
Ala Glu Asp Leu Leu Asp Leu Leu Cys Glu Asn Leu Gly Leu Glu Lys
        130                 135                 140

GGG TAC TTG AAG AAA GTT TTT CAT GGA ACA AAA GGT CCA ACC TTT GGG      479
Gly Tyr Leu Lys Lys Val Phe His Gly Thr Lys Gly Pro Thr Phe Gly
        145                 150                 155

ACT AAG GTG AGC AAC TAT CCA GCT TGT CCT AAG CCA GAG ATG ATC AAA      527
Thr Lys Val Ser Asn Tyr Pro Ala Cys Pro Lys Pro Glu Met Ile Lys
160                 165                 170                 175

GGT CTT AGG GCC CAC ACT GAT GCA GGA GGC ATC ATC TTG TTG TTT CAA      575
Gly Leu Arg Ala His Thr Asp Ala Gly Gly Ile Ile Leu Leu Phe Gln
                180                 185                 190

GAT GAC AAG GTC AGT GGT CTC CAG CTT CTT AAA GAT GGT GAC TGG ATT      623
Asp Asp Lys Val Ser Gly Leu Gln Leu Leu Lys Asp Gly Asp Trp Ile
            195                 200                 205

GAT GTT CCT CCA CTC AAC CAC TCT ATT GTC ATC AAT CTT GGT GAC CAA      671
Asp Val Pro Pro Leu Asn His Ser Ile Val Ile Asn Leu Gly Asp Gln
        210                 215                 220

CTT GAG GTG ATA ACC AAC GGC AGG TAC AAG AGT GTG ATG CAT CGT GTG      719
Leu Glu Val Ile Thr Asn Gly Arg Tyr Lys Ser Val Met His Arg Val
        225                 230                 235

GTG ACT CAG AAA GAA GGA AAC AGA ATG TCA ATT GCA TCT TTC TAC AAC      767
Val Thr Gln Lys Glu Gly Asn Arg Met Ser Ile Ala Ser Phe Tyr Asn
240                 245                 250                 255

CCG GGA AGC GAT GCT GAG ATC TCT CCA GCT TCA TCG CTT GCC TGT AAA      815
Pro Gly Ser Asp Ala Glu Ile Ser Pro Ala Ser Ser Leu Ala Cys Lys
                260                 265                 270

GAA ACC GAG TAC CCA AGT TTT GTT TTT GAT GAC TAC ATG AAG CTC TAT      863
Glu Thr Glu Tyr Pro Ser Phe Val Phe Asp Asp Tyr Met Lys Leu Tyr
            275                 280                 285

GCT GGG GTC AAG TTT CAG CCT AAG GAG CCA CGG TTC GAG GCA ATG AAG      911
```

```
Ala Gly Val Lys Phe Gln Pro Lys Glu Pro Arg Phe Glu Ala Met Lys
        290                 295                 300

AAT GCT AAT GCA GTT ACA GAA TTG AAC CCA ACA GCA GCC GTA GAG ACT      959
Asn Ala Asn Ala Val Thr Glu Leu Asn Pro Thr Ala Ala Val Glu Thr
        305                 310                 315

TTC TAAAAACACC ATGG                                                  976
Phe
320
```

(2) INFORMATION FOR SEQ ID NO:3:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer
            RMM389"

(iii) HYPOTHETICAL: NO (iv) ANTI-SENSE: NO (xi) SEQUENCE DESCRIPTION: SEQ ID NO:3:

GAGAGAGCCA TGGAGAAGAA CATTAAGTTT CCAG                                 34

(2) INFORMATION FOR SEQ ID NO:4:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer
            RMM391"

(iii) HYPOTHETICAL: NO (iv) ANTI-SENSE: NO (xi) SEQUENCE DESCRIPTION: SEQ ID NO:4:

CGGCATCTCT GAAAGATTTT TGTGGATCCT CAAACTCGC                            39

(2) INFORMATION FOR SEQ ID NO:5:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer
            RMM480"

(iii) HYPOTHETICAL: NO (iv) ANTI-SENSE: NO (xi) SEQUENCE DESCRIPTION: SEQ ID NO:5:

CGGCATCTCT GAAAGATTTT TGTGGTACCT CAAA                                 34

(2) INFORMATION FOR SEQ ID NO:6:

(i) SEQUENCE CHARACTERISTICS:
        (A) LENGTH: 96 base pairs (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer
            RMM470"

(iii) HYPOTHETICAL: NO (iv) ANTI-SENSE: NO (xi) SEQUENCE DESCRIPTION: SEQ ID NO:6:

GAGAGCCATG GAGAAGAACA TTAAGTTTCC AGTTGTAGAC TTGTCCAAGC TCATTGGTGA     60

AGAGAGAGAC CAAACAATGG CTTTGATCAA CGATGC                              96

(2) INFORMATION FOR SEQ ID NO:7:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotide Primer
            RMM390"

(iii) HYPOTHETICAL: NO (iv) ANTI-SENSE: NO (xi) SEQUENCE DESCRIPTION: SEQ ID NO:7:

CCGCCAATTA ACAACCAGGT ACCACAAATT TCACACCC                             38

(2) INFORMATION FOR SEQ ID NO:8:

(i) SEQUENCE CHARACTERISTICS:
        (A) LENGTH: 1772 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:8:

GAGAGAGAGC CATGGAGAAG AACATTAAGT TTCCAGTTGT AGACTTGTCC AAGCTCATTG     60

GTGAAGAGAG AGACCAAACC ATGGCTTTGA TCAACGATGC TTGTGAGAAT TGGGGCTTCT    120

TTGAGGTACA AGCATATATG TGATTATATC TAGCTTTTTT GAGTTTGTGT ACTTAATTGG    180

TAATGTGGAT CTTTTTGTTT GGTGGTTAAC TTGATTTTCC AGATAGTGAA CCATGGTTTA    240

CCACATGATT TGATGGACAA CGTCGAGAAG ATGACAAAGG AACATTACAA GATATCAATG    300

GAACAAAAGT TCAACGACAT GCTCAAATCA AAAGGTTTGG AAAATCTTGA GAGAAGTT     360

GAGGATGTTG ATTGGGAAAG CACTTTCTAC CTTCGTCATC TCCCTCAGTC CAATCTCTAC    420

GACATTCCTG ATATGTCTGA TGAATACCGG TACATATATA TTTTTTCTTC ATAAAATCAA    480

CTTTAAATCA TATGTTATGG TAACCAAAAA ATATCATATG TTATATCCCC TTTAAAGGG     540

CCACTCTGCC ACTTTTACCT ATATTAAAAA GATTTTGTG ATATTTTATT TCTAAACAAA    600

ATAACTATAC TTTGTTAGTT AGTAAAAACA GTTTTAAGGA ATTTGTTTCA CTTTAGAACC    660

TCTAATCCTT TTTGTGTAAT GAAAATAAAG TTGAGAAGAA ACGTCTAAAA ATTTAACACA    720

```
CTTATTTGAA AGAGGCATAC TGAAATGTTT TTATTTTGCA GGACGGCCAT GAAAGATTTT      780

GGGAAGAGAT TGGAGAATCT TGCTGAGGAT TTGTTGGATC TATTGTGTGA GAATTTAGGG      840

TTAGAGAAAG GGTACTTGAA GAAAGTTTTT CATGGAACAA AAGGTCCAAC CTTTGGGACT      900

AAGGTGAGCA ACTATCCAGC TTGTCCTAAG CCAGAGATGA TCAAAGGTCT TAGGGCCCAC      960

ACTGATGCAG GAGGCATCAT CTTGTTGTTT CAAGATGACA AGGTCAGTGG TCTCCAGCTT     1020

CTTAAAGATG GTGACTGGAT TGATGTTCCT CCACTCAACC ACTCTATTGT CATCAATCTT     1080

GGTGACCAAC TTGAGGTATG ATATGTTCAC ACCACATTTT CAAAAAAATC TCTTGTTAAA     1140

AAATCCAATG TTCGGTATTG AGTATTGGTT TGGTTCGGGT TTGATGTAAC TGGGAAAAAT     1200

GATTAGTAAA TGTTATAACA GAGCTTATTA AACTAGAAGA GCAACGTTTC CAACCTCAAA     1260

TGGCTTTGGG ACATTCATTT GTATTGTTCT CAAATGGTTT CTTTGGAAAA GGCTAAGGTT     1320

TAACTGGAAA ATATTTTCCT TATTGAATGT AGGTGATAAC CAACGGCAGG TACAAGAGTG     1380

TGATGCATCG TGTGGTGACT CAGAAAGAAG GAAACAGAAT GTCAATTGCA TCTTTCTACA     1440

ACCCGGGAAG CGATGCTGAG ATCTCTCCAG CTTCATCGCT TGCCTGTAAA GAAACCGAGT     1500

ACCCAAGTTT TGTTTTTGAT GACTACATGA AGCTCTATGC TGGGGTCAAG TTTCAGCCTA     1560

AGGAGCCACG GTTCGAGGCA ATGAAGAATG CTAATGCAGT TACAGAATTG AACCCAACAG     1620

CAGCCGTAGA GACTTTCTAA AAACACCTAG GAGTTTGAGC GAAACGAAAG AAACAAAAAT     1680

GTGTTTGTGT TGTGTGTTTA CGTCAATAAG TTAAAGACTG ATATTATTGT TGATATAATT     1740

AAGATGTCTG GCGGTTAATT GTTGGTCCAT GG                                   1772

(2) INFORMATION FOR SEQ ID NO:9:

(i) SEQUENCE CHARACTERISTICS:
        (A) LENGTH: 1275 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Brassica junea
        (C) INDIVIDUAL ISOLATE: India Mustard (ix) FEATURE:
        (A) NAME/KEY: CDS
        (B) LOCATION: 64..1023

(x) PUBLICATION INFORMATION:
        (A) AUTHORS: Pua, Eng-Chong
              Sim, Guek-Eng
              Chye, Mee-Len
        (B) TITLE: Isolation and sequence analaysis of a cDNA
              clone encoding ethylene-forming enzyme in Brassica
              juncea (L.) Czern & Coss
        (C) JOURNAL: Plant Mol. Biol.
        (D) VOLUME: 19
        (F) PAGES: 541-544
        (G) DATE: 1992
        (K) RELEVANT RESIDUES IN SEQ ID NO:9: FROM 1 TO 1275

(xi) SEQUENCE DESCRIPTION: SEQ ID NO:9:

CCCGGGAAAA CAATCAAACA ACTAGCTACT TCAACCAAAT ACTTTCAAAG AAGAGAGAGA       60

GAG ATG GAG AAG AAC ATT AAG TTT CCA GTT GTA GAC TTG TCC AAG CTC       108
    Met Glu Lys Asn Ile Lys Phe Pro Val Val Asp Leu Ser Lys Leu
```

```
              1                  5                     10                       15
ATT GGT GAA GAG AGA GAC CAA ACC ATG GCT TTG ATC AAC GAT GCT TGT              156
Ile Gly Glu Glu Arg Asp Gln Thr Met Ala Leu Ile Asn Asp Ala Cys
                         20                  25                  30

GAG AAT TGG GGC TTC TTT GAG ATA GTG AAC CAT GGT TTA CCA CAT GAT              204
Glu Asn Trp Gly Phe Phe Glu Ile Val Asn His Gly Leu Pro His Asp
                35                  40                  45

TTG ATG GAC AAC GCC GAG AAG ATG ACA AAG GAA CAT TAC AAG ATA TCA              252
Leu Met Asp Asn Ala Glu Lys Met Thr Lys Glu His Tyr Lys Ile Ser
        50                  55                  60

ATG GAA CAA AAG TTC AAC GAC ATG CTC AAA TCC AAA GGT TTG GAA AAT              300
Met Glu Gln Lys Phe Asn Asp Met Leu Lys Ser Lys Gly Leu Glu Asn
    65                  70                  75

CTT GAG CGA GAA GTT GAG GAT GTT GAT TGG GAA AGC ACT TTC TAC CTT              348
Leu Glu Arg Glu Val Glu Asp Val Asp Trp Glu Ser Thr Phe Tyr Leu
80                  85                  90                      95

CGT CAT CTC CCT CAG TCC AAT CTC TAC GAC ATT CCT GAT ATG TCT GAT              396
Arg His Leu Pro Gln Ser Asn Leu Tyr Asp Ile Pro Asp Met Ser Asp
                    100                 105                 110

GAA TAC CGG ACG GCC ATG AAA GAT TTT GGT AAG AGA TTG GAG AAT CTT              444
Glu Tyr Arg Thr Ala Met Lys Asp Phe Gly Lys Arg Leu Glu Asn Leu
            115                 120                 125

GCT GAG GAT TTG TTG GAT CTA TTG TGT GAG AAT TTA GGG TTA GAG AAA              492
Ala Glu Asp Leu Leu Asp Leu Leu Cys Glu Asn Leu Gly Leu Glu Lys
        130                 135                 140

GGG TAC TTG AAG AAA GTG TTT CAT GGA ACA AAA GGT CCA ACC TTT GGG              540
Gly Tyr Leu Lys Lys Val Phe His Gly Thr Lys Gly Pro Thr Phe Gly
    145                 150                 155

ACT AAG GTG AGC AAC TAT CCA GCT TGT CCT AAG CCA GAG ATG ATA AAA              588
Thr Lys Val Ser Asn Tyr Pro Ala Cys Pro Lys Pro Glu Met Ile Lys
160                 165                 170                 175

GGT CTT AGG GCC CAC ACT GAT GCA GGA GGC ATC ATC TTG TTG TTT CAA              636
Gly Leu Arg Ala His Thr Asp Ala Gly Gly Ile Ile Leu Leu Phe Gln
                    180                 185                 190

GAT GAC AAG GTC ACT GGT CTC CAG CTT CTT AAA GAT GGT GAC TGG ATT              684
Asp Asp Lys Val Thr Gly Leu Gln Leu Leu Lys Asp Gly Asp Trp Ile
            195                 200                 205

GAT GTT CCT CCA CTC AAC CAC TCT ATT GTC ATC AAT CTT GGT GAC CAA              732
Asp Val Pro Pro Leu Asn His Ser Ile Val Ile Asn Leu Gly Asp Gln
        210                 215                 220

CTT GAG GTG ATA ACT AAC GGC AGG TAC AAG AGT ATG ATG CAC CGT GTG              780
Leu Glu Val Ile Thr Asn Gly Arg Tyr Lys Ser Met Met His Arg Val
    225                 230                 235

GTG ACT CAG AAA GAA GGA AAC AGA ATG TCA ATT GCA TCT TTC TAC AAC              828
Val Thr Gln Lys Glu Gly Asn Arg Met Ser Ile Ala Ser Phe Tyr Asn
240                 245                 250                 255

CCG GGA AGC GAT GCT GAG ATC TCT CCA GCT TCA TCG CTT GCC TGT AAA              876
Pro Gly Ser Asp Ala Glu Ile Ser Pro Ala Ser Ser Leu Ala Cys Lys
                    260                 265                 270

GAA ACC GAG TAC CCG AGT TTT GTT TTT GAT GAC TAC ATG AAG CTC TAT              924
Glu Thr Glu Tyr Pro Ser Phe Val Phe Asp Asp Tyr Met Lys Leu Tyr
            275                 280                 285

GCT GGG GTC AAG TTT CAG CCT AAG GAG CCA CGC TTC GAG GCA ATG AAG              972
Ala Gly Val Lys Phe Gln Pro Lys Glu Pro Arg Phe Glu Ala Met Lys
        290                 295                 300

AAT GCT AAT GCA GTT ACG GAA TTG AAC CCA ACA GCA GCC GTA GAG ACT             1020
Asn Ala Asn Ala Val Thr Glu Leu Asn Pro Thr Ala Ala Val Glu Thr
    305                 310                 315

TTC TAAAAACAAA GTGGAGTTTG AGCGAAAGCA ACAAACAAAA ATGTGTTTTG                  1073
```

Phe
320

```
TGTTGTGTGT TTACGTCAAT AAGTTAAAGA CTGATATTAT TGTTGATATA ATTAAGATGT    1133

CTGGCGGTTA ATTGTTGGTC AATGGTGTTT AAAGTGTGGG GTGTTTATTT ATGTTTATGG    1193

AAGATGATAA TAATAAAAAT AAATAATATG ATAACTGTTC TAAGAAAAAA AAAAAAAAAA    1253

AAAACCCGGG CCCGGGCCCG GG                                             1275
```

(2) INFORMATION FOR SEQ ID NO:10:

(i) SEQUENCE CHARACTERISTICS:
        (A) LENGTH: 320 amino acids
        (B) TYPE: amino acid
        (D) TOPOLOGY: linear (ii) MOLECULE TYPE: protein (xi) SEQUENCE DESCRIPTION: SEQ ID NO:10:

```
Met Glu Lys Asn Ile Lys Phe Pro Val Val Asp Leu Ser Lys Leu Ile
 1               5                  10                  15

Gly Glu Glu Arg Asp Gln Thr Met Ala Leu Ile Asn Asp Ala Cys Glu
            20                  25                  30

Asn Trp Gly Phe Phe Glu Ile Val Asn His Gly Leu Pro His Asp Leu
        35                  40                  45

Met Asp Asn Ala Glu Lys Met Thr Lys Glu His Tyr Lys Ile Ser Met
50                  55                  60

Glu Gln Lys Phe Asn Asp Met Leu Lys Ser Lys Gly Leu Glu Asn Leu
65                  70                  75                  80

Glu Arg Glu Val Glu Asp Val Asp Trp Glu Ser Thr Phe Tyr Leu Arg
                85                  90                  95

His Leu Pro Gln Ser Asn Leu Tyr Asp Ile Pro Asp Met Ser Asp Glu
            100                 105                 110

Tyr Arg Thr Ala Met Lys Asp Phe Gly Lys Arg Leu Glu Asn Leu Ala
        115                 120                 125

Glu Asp Leu Leu Asp Leu Leu Cys Glu Asn Leu Gly Leu Glu Lys Gly
130                 135                 140

Tyr Leu Lys Lys Val Phe His Gly Thr Lys Gly Pro Thr Phe Gly Thr
145                 150                 155                 160

Lys Val Ser Asn Tyr Pro Ala Cys Pro Lys Pro Glu Met Ile Lys Gly
                165                 170                 175

Leu Arg Ala His Thr Asp Ala Gly Gly Ile Ile Leu Leu Phe Gln Asp
            180                 185                 190

Asp Lys Val Thr Gly Leu Gln Leu Leu Lys Asp Gly Asp Trp Ile Asp
        195                 200                 205

Val Pro Pro Leu Asn His Ser Ile Val Ile Asn Leu Gly Asp Gln Leu
210                 215                 220

Glu Val Ile Thr Asn Gly Arg Tyr Lys Ser Met Met His Arg Val Val
225                 230                 235                 240

Thr Gln Lys Glu Gly Asn Arg Met Ser Ile Ala Ser Phe Tyr Asn Pro
                245                 250                 255

Gly Ser Asp Ala Glu Ile Ser Pro Ala Ser Ser Leu Ala Cys Lys Glu
            260                 265                 270

Thr Glu Tyr Pro Ser Phe Val Phe Asp Asp Tyr Met Lys Leu Tyr Ala
        275                 280                 285

Gly Val Lys Phe Gln Pro Lys Glu Pro Arg Phe Glu Ala Met Lys Asn
290                 295                 300
```

```
       Ala Asn Ala Val Thr Glu Leu Asn Pro Thr Ala Ala Val Glu Thr Phe
       305                 310                 315                 320

(2) INFORMATION FOR SEQ ID NO:11:

(i) SEQUENCE CHARACTERISTICS:
         (A) LENGTH: 1772 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: intron
         (B) LOCATION: 125..221

(ix) FEATURE:
         (A) NAME/KEY: intron
         (B) LOCATION: 451..762

(ix) FEATURE:
         (A) NAME/KEY: intron
         (B) LOCATION: 1097..1354

(xi) SEQUENCE DESCRIPTION: SEQ ID NO:11:

GAGAGAGAGC CATGGAGAAG AACATTAAGT TTCCAGTTGT AGACTTGTCC AAGCTCATTG         60

GTGAAGAGAG AGACCAAACC ATGGCTTTGA TCAACGATGC TTGTGAGAAT TGGGGCTTCT        120

TTGAGGTACA AGCATATATG TGATTATATC TAGCTTTTTT GAGTTTGTGT ACTTAATTGG        180

TAATGTGGAT CTTTTTGTTT GGTGGTTAAC TTGATTTTCC AGATAGTGAA CCATGGTTTA        240

CCACATGATT TGATGGACAA CGTCGAGAAG ATGACAAAGG AACATTACAA GATATCAATG        300

GAACAAAAGT TCAACGACAT GCTCAAATCA AAAGGTTTGG AAAATCTTGA GAGAGAAGTT        360

GAGGATGTTG ATTGGGAAAG CACTTTCTAC CTTCGTCATC TCCCTCAGTC CAATCTCTAC        420

GACATTCCTG ATATGTCTGA TGAATACCGG TACATATATA TTTTTTCTTC ATAAAATCAA        480

CTTTAAATCA TATGTTATGG TAACCAAAAA ATATCATATG TTATATCCCC TTTAAAAGGG        540

CCACTCTGCC ACTTTTACCT ATATTAAAAA GATTTTGTG ATATTTATT TCTAAACAAA         600

ATAACTATAC TTTGTTAGTT AGTAAAAACA GTTTTAAGGA ATTTGTTTCA CTTTAGAACC        660

TCTAATCCTT TTTGTGTAAT GAAAATAAAG TTGAGAAGAA ACGTCTAAAA ATTTAACACA        720

CTTATTTGAA AGAGGCATAC TGAAATGTTT TTATTTTGCA GGACGGCCAT GAAAGATTTT        780

GGGAAGAGAT TGGAGAATCT TGCTGAGGAT TTGTTGGATC TATTGTGTGA GAATTTAGGG        840

TTAGAGAAAG GGTACTTGAA GAAAGTTTTT CATGGAACAA AAGGTCCAAC CTTTGGGACT        900

AAGGTGAGCA ACTATCCAGC TTGTCCTAAG CCAGAGATGA TCAAAGGTCT TAGGGCCCAC        960

ACTGATGCAG GAGGCATCAT CTTGTTGTTT CAAGATGACA AGGTCAGTGG TCTCCAGCTT       1020

CTTAAAGATG GTGACTGGAT TGATGTTCCT CCACTCAACC ACTCTATTGT CATCAATCTT       1080

GGTGACCAAC TTGAGGTATG ATATGTTCAC ACCACATTTT CAAAAAAATC TCTTGTTAAA       1140

AAATCCAATG TTCGGTATTG AGTATTGGTT TGGTTCGGGT TTGATGTAAC TGGGAAAAAT       1200

GATTAGTAAA TGTTATAACA GAGCTTATTA AACTAGAAGA GCAACGTTTC CAACCTCAAA       1260

TGGCTTTGGG ACATTCATTT GTATTGTTCT CAAATGGTTT CTTTGGAAAA GGCTAAGGTT       1320

TAACTGGAAA ATATTTTCCT TATTGAATGT AGGTGATAAC CAACGGCAGG TACAAGAGTG       1380

TGATGCATCG TGTGGTGACT CAGAAAGAAG GAAACAGAAT GTCAATTGCA TCTTTCTACA       1440

ACCCGGGAAG CGATGCTGAG ATCTCTCCAG CTTCATCGCT TGCCTGTAAA GAAACCGAGT       1500
```

```
ACCCAAGTTT TGTTTTTGAT GACTACATGA AGCTCTATGC TGGGGTCAAG TTTCAGCCTA      1560

AGGAGCCACG GTTCGAGGCA ATGAAGAATG CTAATGCAGT TACAGAATTG AACCCAACAG      1620

CAGCCGTAGA GACTTTCTAA AAACAAAGTG GAGTTTGAGC GAAACGAAAG AAACAAAAAT      1680

GTGTTTGTGT TGTGTGTTTA CGTCAATAAG TTAAAGACTG ATATTATTGT TGATATAATT      1740

AAGATGTCTG GCGGTTAATT GTTGGTCCAT GG                                    1772

(2) INFORMATION FOR SEQ ID NO:12:

(i) SEQUENCE CHARACTERISTICS:
        (A) LENGTH: 992 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GAGAGAGAGC CATGGAGAAG AACATTAAGT TTCCAGTTGT AGACTTGTCC AAGCTCATTG        60

GTGAAGAGAG AGACCAAACC ATGGCTTTGA TCAACGATGC TTGTGAGAAT TGGGGCTTCT       120

TTGAGATAGT GAACCATGGT TTACCACATG ATTTGATGGA CAACGTCGAG AAGATGACAA       180

AGGAACATTA CAAGATATCA ATGGAACAAA AGTTCAACGA CATGCTCAAA TCAAAAGGTT       240

TGGAAAATCT TGAGAGAGAA GTTGAGGATG TTGATTGGGA AAGCACTTTC TACCTTCGTC       300

ATCTCCCTCA GTCCAATCTC TACGACATTC CTGATATGTC TGATGAATAC CGGACGGCCA       360

TGAAAGATTT TGGGAAGAGA TTGGAGAATC TTGCTGAGGA TTTGTTGGAT CTATTGTGTG       420

AGAATTTAGG GTTAGAGAAA GGGTACTTGA AGAAAGTTTT TCATGGAACA AAAGGTCCAA       480

CCTTTGGGAC TAAGGTGAGC AACTATCCAG CTTGTCCTAA GCCAGAGATG ATCAAAGGTC       540

TTAGGGCCCA CACTGATGCA GGAGGCATCA TCTTGTTGTT TCAAGATGAC AAGGTCAGTG       600

GTCTCCAGCT TCTTAAAGAT GGTGACTGGA TTGATGTTCC TCCACTCAAC CACTCTATTG       660

TCATCAATCT TGGTGACCAA CTTGAGGTGA TAACCAACGG CAGGTACAAG AGTGTGATGC       720

ATCGTGTGGT GACTCAGAAA GAAGGAAACA GAATGTCAAT TGCATCTTTC TACAACCCGG       780

GAAGCGATGC TGAGATCTCT CCAGCTTCAT CGCTTGCCTG TAAAGAAACC GAGTACCCAA       840

GTTTTGTTTT TGATGACTAC ATGAAGCTCT ATGCTGGGGT CAAGTTTCAG CCTAAGGAGC       900

CACGGTTCGA GGCAATGAAG AATGCTAATG CAGTTACAGA ATTGAACCCA ACAGCAGCCG       960

TAGAGACTTT CTAAAAACAC CTAGGAGTTT GA                                    992

(2) INFORMATION FOR SEQ ID NO:13:

(i) SEQUENCE CHARACTERISTICS:
        (A) LENGTH: 995 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GAGAGAGAGC CATGGAGAAG AACATTAAGT TTCCAGTTGT AGACTTGTCC AAGCTCATTG        60

GTGAAGAGAG AGACCAAACC ATGGCTTTGA TCAACGATGC TTGTGAGAAT TGGGGCTTCT       120

TTGAGATAGT GAACCATGGT TTACCACATG ATTTGATGGA CAACGTCGAG AAGATGACAA       180

AGGAACATTA CAAGATATCA ATGGAACAAA AGTTCAACGA CATGCTCAAA TCAAAAGGTT       240

TGGAAAATCT TGAGAGAGAA GTTGAGGATG TTGATTGGGA AAGCACTTTC TACCTTCGTC       300
```

```
ATCTCCCTCA GTCCAATCTC TACGACATTC CTGATATGTC TGATGAATAC CGGACGGCCA      360

TGAAAGATTT TGGGAAGAGA TTGGAGAATC TTGCTGAGGA TTTGTTGGAT CTATTGTGTG      420

AGAATTTAGG GTTAGAGAAA GGGTACTTGA AGAAAGTTTT TCATGGAACA AAAGGTCCAA      480

CCTTTGGGAC TAAGGTGAGC AACTATCCAG CTTGTCCTAA GCCAGAGATG ATCAAAGGTC      540

TTAGGGCCCA CACTGATGCA GGAGGCATCA TCTTGTTGTT TCAAGATGAC AAGGTCAGTG      600

GTCTCCAGCT TCTTAAAGAT GGTGACTGGA TTGATGTTCC TCCACTCAAC CACTCTATTG      660

TCATCAATCT TGGTGACCAA CTTGAGGTGA TAACCAACGG CAGGTACAAG AGTGTGATGC      720

ATCGTGTGGT GACTCAGAAA GAAGGAAACA GAATGTCAAT TGCATCTTTC TACAACCCGG      780

GAAGCGATGC TGAGATCTCT CCAGCTTCAT CGCTTGCCTG TAAAGAAACC GAGTACCCAA      840

GTTTTGTTTT TGATGACTAC ATGAAGCTCT ATGCTGGGGT CAAGTTTCAG CCTAAGGAGC      900

CACGGTTCGA GGCAATGAAG AATGCTAATG CAGTTACAGA ATTGAACCCA ACAGCAGCCG      960

TAGAGACTTT CTAAAAACAC CTAGGAGTTT GAGCG                                995

(2) INFORMATION FOR SEQ ID NO:14:

(i) SEQUENCE CHARACTERISTICS:
        (A) LENGTH: 1230 base pairs
        (B) TYPE: nucleic acid
        (C) STRANDEDNESS: single
        (D) TOPOLOGY: linear (xi) SEQUENCE DESCRIPTION: SEQ ID NO:14:

GCACAAACCA AATCTTGTAT CTACAAAAAG AAATGGCTGT CTTTCCTATC ATCAACTTGG       60

AAAACATCAA TGATGATGGT AGAGCTAAGA TATTGGAGCA AATTGAAGAT GCCTGCCAAA      120

ATTGGGGTTT CTTTGAGTTG GTGAACCATG GGATCCCACA TGAGTTTTTA GACATGGTGG      180

AGAAGATGAC AAGAGATCAT TACAAGAAAT GTATGGAAGA GAGGTTTAAG GAGACTGTGC      240

TTAGCAAAGG CTTAGAGGCT GCACAAGCTG AAGTTAATGA TATGGATTGG GAAAGCACCT      300

TTTTCTTACG CCATCTTCCT GAATCAAACA TCTCCCAGAT GTCTGATCTC GACGAGGAGT      360

ATAAGAAAAT TATGAAGGAA TTTGCGAAGA AATTGGAGAA TCTTGCTGAG GAGTTGTTGG      420

ACCTGCTATG TGAGAATCTT GGGTTGGAGA AGGGTTATCT CAAAAAGGCT TTCTATGGTT      480

CAAAAGGTCC TACATTTGGA ACAAAGGTGA GCAATTATCC GCCGTGTCCC AAGCCGGACC      540

TCATCAAGGG TCTTCGAGCC CACACCGACG CCGGTGGCAT CATCCTCCTC TTCCAAGATG      600

ACAAGGTAAG TGGCCTGCAA CTCCTGAAAG ATGGCAACTG GATCGACGTG CCCCCAATGC      660

GCCACGCCAT TGTCGTCAAC CTCGGGGACC AACTTGAGGT GATCACAAAT GGAAGATACA      720

AAAGTGTGAT GCATAGAGTG TTAACTCAAA CGAGTGGAAC TGGGCGAATG TCGATAGCTT      780

CATTCTACAA TCCGGGGAGC GACGCGGTGA TCTACCCGGC GCCGGCGCTA GTGGAGAAAG      840

ATCAGGATGA GGAGAAGAAG GAAGTGTACC CCAAGTTTGT GTTTGAAGAT TACATGAAGC      900

TGTATCTAGG AGTGAAGTTT CAGGCGAAGG AGCCAAGATT TGAAGCCATG AAAGCCAATG      960

CTAATTTGGG TCCAATGGCA ACAGCATAAT TAAAACACCC ACTTTTTCAT TAATAGTAAT     1020

AAGGAATATT AGAGGGCTTG TGTTTGCCCT TTTTAAGTGG GTCATCATTA TTGTTATTAA     1080

ATTTAGTGAA AAGTCAAAAC CAAATATATA AATATACATA TATATATATA TGTTTGGTAA     1140

TTGTAGCAAC TTAATAGGCT AAAAGCTAGT ATAAGGATTA AGGAGTCTTG TTCTCAATTT     1200

TCTTTATAAT TTAAATTCAC TTTCAGCTTA                                     1230
```

It is claimed:

1. An isolated and purified DNA comprising a nucleic acid sequence encoding a *Brassica oleracea* ACC oxidase polypeptide.

2. A DNA isolate comprising an isolated and purified nucleic acid which encodes a *Brassica oleracea* protein, comprising a nucleotide sequence selected from the group consisting of:

the nucleotide sequence as shown in SEQ ID NO:2;

the nucleotide sequence as shown in SEQ ID NO:8; and the nucleotide sequence which encodes the same sequence of amino acids as encoded by the nucleotide sequence shown in SEQ ID NO:2 or SEQ ID NO:8.

3. A plant transformation vector comprising a DNA isolate as recited in claim 1, a promoter, and a polyadenylation signal, wherein said promoter is upstream and operably linked to said DNA isolate, and said DNA isolate is upstream and operably linked to said polyadenylation signal.

4. A plant transformation vector according to claim 3 wherein said promoter is Cauliflower mosaic virus 35S promoter.

5. A plant transformation vector according to claim 4 wherein said polyadenylation signal is the polyadenylation signal of the cauliflower mosaic CaMV 35S gene.

6. A bacterial cell comprising the plant transformation vector of claim 5.

7. A bacterial cell of claim 6 in which said bacterial cell is selected from the group consisting of an *Agrobacterium tumefaciens* cell and an *Agrobacterium rhizogenes* cell.

8. A transformed plant cell comprising the plant transformation vector of claim 3.

9. A transformed plant cell of claim 8 wherein the promoter and polyadenylation signal are each from the cauliflower mosaic virus 35S gene.

10. A transformed *Brassica oleracea L.* comprising at least one transformed plant cell of claim 9.

11. A transformed plant seed comprising the plant transformation vector of claim 3.

12. A transformed plant cell of claim 11 wherein the promoter and polyadenylation signal are each from the cauliflower mosaic virus 35S gene.

13. A transgenic *Brassica oleracea L.* grown from transformed plant seed of claim 12.

14. A method of producing a recombinant *Brassica oleracea* ACC oxidase polypeptide the method comprising the steps of:

(a) providing a cell transformed with DNA encoding a *Brassica oleracea* ACC polypeptide positioned for expression in said cell;

(b) culturing said transformed cell under conditions for expressing said DNA, and (c) isolating said recombinant *Brassica oleracea* ACC oxidase polypeptide.

* * * * *